United States Patent [19]

Ernst et al.

[11] Patent Number: 5,342,929
[45] Date of Patent: Aug. 30, 1994

[54] PROCESS FOR THE PREPARATION OF GLYCOSIDES

[75] Inventors: Beat Ernst, Magden, Switzerland; Michael Heneghan, Salford, England; Andreas Hafner, Frenkendorf, Switzerland

[73] Assignee: Ciba-Geigy Corporation, Ardsley, N.Y.

[21] Appl. No.: 937,818

[22] Filed: Aug. 31, 1992

[30] Foreign Application Priority Data

Sep. 4, 1991 [CH] Switzerland .................... 2603/91

[51] Int. Cl.$^5$ .................... C07H 15/04; C07H 17/00
[52] U.S. Cl. .................... 536/18.6; 536/4.1; 536/17.2; 536/17.6; 536/18.1; 536/18.2; 536/18.5
[58] Field of Search .................... 536/17.6, 186, 17.2, 536/4.1, 18.1, 18.2, 18.5, 18.6

[56] References Cited

U.S. PATENT DOCUMENTS

| | | | |
|---|---|---|---|
| 3,972,868 | 8/1976 | Avela | 536/18 |
| 4,675,392 | 6/1987 | Dahmen et al. | 536/17.6 |
| 4,749,785 | 6/1988 | Thiem et al. | 536/18.6 |
| 4,868,289 | 9/1989 | Magnusson et al. | 536/4.1 |

FOREIGN PATENT DOCUMENTS 168723 1/1986 European Pat. Off. .

OTHER PUBLICATIONS

Angew Chem. 98 pp. 213–236 (1986).
Chem. Ber. 26, pp. 2400–2412 (1893).
Chem. Ber. 28, pp. 145–1167 (1895).
Chem. Soc. Rev. 13, pp. 15–45 (1984).
Bartholome' et al. "Ullmanns Encyklop adie der technischen Chemie, Band 16" pp. 587–607 4. Auflage, 1978 Verlag Chemie.
J. Amer. Chem. Soc. 107, 5556 (1985).
Chem. Ber. 34, 957 (1901).
Angew. Chemie,. Int. Ed. Engl. 25, 725 (1986).

*Primary Examiner*—Herbert J. Lilling
*Attorney, Agent, or Firm*—George R. Dohmann; Kevin T. Mansfield

[57] ABSTRACT

The invention relates to a process for the preparation of glycosides by reacting protected sugars carrying an anomeric hydroxyl group with an aglycon selected from the group consisting of alcohol, thiol and a protected sugar carrying a non-anomeric hydroxyl group, in an inert solvent, in the preferred temperature range from −20° to +250° C., in the presence of catalytic amounts of metal complex salts. The glycosides are obtained in high yield. Often an excess of the α- or β-form is obtained and even the pure α- oder β-forms are obtainable.

62 Claims, No Drawings

PROCESS FOR THE PREPARATION OF GLYCOSIDES

The present invention relates to a process for the preparation of glycosides by reacting protected sugars carrying an anomeric hydroxyl group with an aglycon selected from the group consisting of alcohol and a protected sugar carrying a non-anomeric hydroxyl group, in an inert solvent in the preferred temperature range from $-20°$ to $+250°$ C., in the presence of catalytic amounts of metal complex salts.

Processes for the preparation of glycosides are known in which initially the anomeric hydroxyl group is activated by substitution with —F [K. C. Nicolaou et al., J. Amer. Chem. Soc. 107, 5556 (1985)], —Br [W. Koenig et al., Chem. Ber. 34, 957 (1901)] or —O—C(=NH)CCl$_3$ [R. R. Schmidt et al., Angew. Chemie, Int. Ed. Engl. 25, 725 (1986)] and is then reacted with an aglycon, conveniently an alcohol, in the presence of Lewis acids or stoichiometric amounts of silver or mercury salts. The complicated synthesis and the physiologically harmful metal salts make these processes unsuitable for industrial production.

The direct glycosilation of the anomeric hydroxyl group of unprotected sugars (D-glucose) with methanol as aglycon is described by E. Fischer et al. in Ber. 26, page 2400, (1893) and Ber. 28, page 1145, (1895). The thermodynamically controlled reaction proceeds relatively slowly and always yields mixtures of methyl-α- and methyl-β-D-glucopyranoside and methyl-α- and -β-D-glucofuranoside.

Surprisingly, it has now been found that the direct glycosilation also leads to the desired glycosides in high yield and relatively short reaction times by the catalytic action of metal complex salts. In addition, large amounts of the α- or β-form are often obtained. Because of the catalytic amounts of metal complexes, there are no ecological risks to carrying out the process on an industrial scale.

Specifically, the invention provides a process for the preparation of glycosides by reacting sugars carrying an anomeric hydroxyl group with an aglycon, which process comprises reacting, in an inert solvent, a protected sugar which carries an anomeric hydroxyl group, with a) an aglycon selected from the group consisting of a) aliphatic alcohols, cycloaliphatic alcohols, aromatic or aromatic-aliphatic alcohols, and b) protected sugars carrying a non-anomeric hydroxyl group either in each case alone or together with an ortho-ester, in the presence of catalytic amounts of a metal complex salt of (1) a metal cation of a metal of the second to fifth main group, of the first to eighth subgroup, or of the lanthanides, of the Periodic Table of the Elements, (2) one or more identical or different monodentate or polydentate ligands in accordance with the co-ordination number of the metal cation, (3) optionally a nucleophilic anion selected from the group consisting of halide, pseudohalide, C$_1$–C$_8$alcoholate or unsubstituted or C$_1$–C$_4$alkyl-substituted phenolate, secondary amido containing 2 to 12 carbon atoms, bis[(tri-C$_1$–C$_6$alkyl)silyl]amido or unsubstituted or C$_1$–C$_4$alkyl-substituted cyclopentadienyl, and (4) a non-nucleophilic anion selected from the group consisting of anion of an oxyacid, BF$_4$, PF$_6$, AsF$_6$ or SbF$_6$ in accordance with the valency of the complexed metal cation.

The sugars used in the novel process are known, can be prepared by known processes, and many are commercially available. They may typically be protected mono- and oligosaccharides, such as mono-, di-, tri-, tetra- and pentasaccharides.

In a preferred embodiment of the process, the protected mono- and oligosaccharides are aldoses or ketoses which carry an anomeric hydroxyl group.

In a particularly preferred embodiment of the invention, the protected monosaccharide is selected from aldopyranoses, aldofuranoses, ketopyranoses or ketofuranoses which carry an anomeric hydroxyl group.

The aldopyranose is preferably selected from the group consisting of D-ribose, D-arabinose, D-xylose, D-lyxose, D-allose, D-altrose, D-glucose, D-mannose, D-gulose, D-iodose, D-galactose and D-talose; the aldofuranose from the group consisting of D-erythrose, D-threose, D-ribose, D-arabinose, D-xylose, D-lyxose, D-allose, D-altrose, D-glucose, D-mannose, D-gulose, D-iodose, D-galactose and D-talose; the ketopyranose from the group consisting of D-piscose, D-fructose, D-sorbose and D-tagatose; and the ketofuranose from the group consisting of D-piscose, D-fructose, D-sorbose and D-tagatose, the hydroxyl groups of which, except for the anomeric hydroxyl group, are protected.

The disaccharide is preferably selected from the group consisting of trehalose, sophorose, kojibiose, laminaribiose, maltose, cellobiose, isomaltose, gentibiose, saccharose, raffinose and lactose, the hydroxyl groups of which, except for the anomeric hydroxyl group, are protected.

Protected mono- and oligosaccharide derivatives carrying an anomeric hydroxyl group are known, are obtainable by known processes, and some are commercially available. They are typically protected deoxy sugars, amino sugars, thiosugars, sugar acids or esters of sugar acids which carry an anomeric hydroxyl group, for example 2-deoxy sugar, 2-thiosugar, 2-amino sugar, gluconic acids and esters, preferably the C$_1$–C$_4$alkyl esters, thereof.

Protected means that the hydroxyl groups of the mono- and oligosaccharides or mono- and oligosaccharide derivatives, except for the anomeric hydroxyl group carrying a removable protective group, are derivatised. Such protective groups and derivatisation processes are commonly known in sugar chemistry. Exemplary of such protective groups are: linear or branched C$_1$–C$_8$alkyl, preferably C$_1$–C$_4$alkyl, typically methyl, ethyl, n-propyl and isopropyl, n-butyl, isobutyl and tert-butyl; C$_7$–C$_{12}$aralkyl, typically benzyl; trialkylsilyl containing 3 to 20, preferably 3 to 12, carbon atoms, typically trimethylsilyl, triethylsilyl, tri-n-propylsilyl, isopropyldimethylsilyl, tert-butyldimethylsilyl, tert-butyldiphenylsilyl, n-octyldimethylsilyl, (1,1,2,2-tetramethylethyl)dimethylsilyl; substituted methylidene groups which are obtainable by acetal or ketal formation of vicinal —OH groups of the sugars or sugar derivatives with aldehydes and ketones, and which preferably contain 2 to 12 and 3 to 12 carbon atoms, respectively, for example C$_1$–C$_{12}$alkylidene, C$_1$–C$_6$alkylidene and, most preferably, C$_1$–C$_4$alkylidene (ethylidene, 1,1- or 2,2-propylidene, 1,1- or 2,2-butylidene) or benzylidene; C$_2$–C$_{12}$acyl, preferably C$_2$–C$_8$acyl, typically acetyl, propanoyl, butanoyl, pentanoyl, hexanoyl and benzoyl; R—SO$_2$—, wherein R is C$_1$–C$_{12}$alkyl, preferably C$_1$–C$_6$alkyl, C$_5$cycloalkyl or C$_6$cycloalkyl, phenyl, benzyl, C$_1$–C$_{12}$alkylphenyl and, preferably, C$_1$–C$_4$alkylphenyl, or C$_1$–C$_{12}$alkylbenzyl, and preferably, C$_1$–C$_4$alkylbenzyl, conveniently methyl-, ethyl-, propyl-, butyl-, phenyl-, benzyl- and p-methylphenylsulfonyl.

The orthoesters are preferably derived from a $C_1$–$C_4$ carboxylic acid, typically from formic acid, acetic acid, propionic acid or butyric acid. Formic acid orthoesters are particularly preferred. Preferred orthoesters are esters of these acids with a linear or branched $C_1$–$C_{20}$alkanol, $C_2$–$C_{20}$alkenol carrying a non-vinylic alcohol group, with a mono- or polycycloaliphatic or a mono- or polycycloheteroaliphatic $C_3$–$C_8$alcohol (containing the hetero atoms O, S and N), with an aromatic $C_6$–$C_{20}$alcohol, or with an aromatic-aliphatic $C_7$–$C_{20}$alcohol which is unsubstituted or substituted by $C_1$–$C_6$alkyl, $C_1$–$C_6$alkoxy or $C_1$–$C_6$alkylthio, phenoxy, $C_1$–$C_4$alkylphenoxy or $C_1$–$C_4$alkoxyphenoxy, benzyl, benzyloxy or $C_1$–$C_4$alkylbenzyloxy or $C_1$–$C_4$alkoxybenzyloxy. Orthoesters with alcohols are preferred.

Illustrative examples of alkanols which preferably contain 1 to 12 carbon atoms are methanol, ethanol, n-propanol and isopropanol, n-butanol, isobutanol or tert-butanol, pentanol, hexanol, heptanol, octanol, nonanol, decanol, undecanol, dodecanol, tetradecanol, hexadecanol, octadecanol and icosanol.

Illustrative examples of alkenols are allyl alcohol, but-1-en-4-ol, but-2-en-4-ol, pent-1- or -2-en-5-ol and hex-1-en-6-ol.

Exemplary of cycloaliphatic alcohols which preferably contain 1 to 4 rings are cyclopropanol, cyclobutanol, cyclopentanol, cyclohexanol, cycloheptanol and cyclooctanol. The cycloaliphatic and cycloheteroaliphatic alcohols may also be the fused ring systems which frequently occur in natural products.

Particularly suitable aromatic alcohols are phenols and naphthols.

Suitable aromatic-aliphatic alcohols are phenyl alkanols which contain preferably 1 to 18, most preferably 1 to 12, carbon atoms in the alkanol group, typically benzyl alcohol, 1-phenylethan-2-ol, 1-phenylpropan-3-ol and 1-phenyloctan-8-ol.

The exemplifed and preferred alcohols may be unsubstituted or substituted as defined above. A preferred group of alcohols for the orthoesters, more particularly for the orthoformates, comprises $C_1$–$C_4$alkanols, allyl alcohol, benzyl alcohol and phenol.

Alcohols suitable for use as aglycon a) are also those cited as being suitable for the orthoesters. The aliphatic alcohols are preferred. A preferred group of aglycons a) comprises alkanols and alkenols containing 1 or 2 to 18, preferably 1 or 2 to 12, carbon atoms, mono- to tetracyclic cycloaliphatics containing 3 to 20, most preferably 5 to 20, carbon atoms, phenol and benzyl alcohol which are unsubstituted or substituted by $C_1$–$C_6$alkyl, $C_1$–$C_6$alkoxy or $C_1$–$C_6$alkylthio, phenoxy, $C_1$–$C_4$alkylphenoxy or $C_1$–$C_4$alkoxyphenoxy, benzyl, benzyloxy or $C_1$–$C_4$alkylbenzyloxy or $C_1$–$C_4$alkoxybenzyloxy.

Suitable aglycons b) are the above mentioned sugars or sugar derivatives the anomeric hydroxyl group of which is protected and which contain a free hydroxyl group. Preferably these sugars contain a hydroxymethyl group. The preferences stated above apply to these sugars and sugar derivatives.

Catalytic amounts will be understood as meaning preferably an amount of 0.01 to 20 mol %, more particularly 0.01 to 15 mol % and, most preferably, 0.01 to 10 mol %, based on the amount of the protected sugar or sugar derivative.

A great number of metal complexes suitable for use in the practice of this invention are known or they can be prepared by known and analogous processes.

The metal complex salts may be mononuclear or polynuclear, typically mono- or binulcear. Preferably the metal complexes are mononuclear. The metal cations are preferably derived from the following metals of the cited groups of the Periodic Table of the Elements: Mg, Ca, Sr, Ba; B, Al, Ga, In; Sn, Pb; Sb, Bi; Cu, Ag, Au; Zn, Cd, Hg; Sc, Y, La; Ti, Zr, Hf; V, Nb, Ta; Cr, Mo, W; Mn; Fe, Co, Ni, Ru, Rh, Pd, Os, Ir, Pt; and the lanthanides Ce, Pr, Nd, Pm, Sm, Eu, Gd, Tb, Dy, Ho, Er, Tm, Yb and Lu. More preferred metal cations are those of the metals Mg, Ca, Sr, B, Al, In, Sn, Pb, Bi, Cu, Ag, Au, Zn, Ti, Zr, Hf, V, Nb, Cr, Mo, W, Mn, Fe, Co, Ni, Ru, Rh, Pd, Ir, Pt, Ce, Nd, Sm, Eu and Yb. Still more preferred are metal cations of the metals Mg, Ca, B, In, Sn, Pb, Cu, Ag, Au, Zn, Ti, Zr, V, Cr, Mo, W, Mn, Fe, Co, Ni, Ru, Rh, Pd, Ir, Pt, Ce, Nd and Yb. More preferred still are metal cations of the metals Mg, B, Sn, Cu, Ag, Zn, Ti, Zr, Mn, Ni, Ru, Rh, Pd, Ir, Pt and Ce. Metal cations of the metals Mg, B, Cu, Ag, Zn, Rh, Pd, Pt, and Ce are most preferred.

The ligand can be non-chiral or chiral. Monodentate to tridentate ligands are preferred. A great number of such ligands are also in described in the literature. The polydentate ligands containing the complex forming groups preferably form with the metal cation a five- to seven-membered ring, more particularly a five- or six-membered ring. The complex forming groups of the polydentate ligands are therefore preferably in the 1,2-, 1,3- or 1,4-positions of a carbon chain containing 2 to 4, most preferably, 2 or 3, carbon atoms, in which case the compounds may be linear or mono- or bicyclic compounds. These compounds may contain 2 to 30, preferably 2 to 20, most preferably 2 to 12, carbon atoms, without the carbon atoms in the complex forming groups.

The ligands may typically be weakly co-ordinating organic ligands which contain 1 to 20, preferably 1 to 12, carbon atoms, and which contain hetero atoms or hetero groups capable of co-ordination, including —OH, —CN, —CHO, —CO—, —O—, —C(O)OR$_0$ and P(O—)$_3$, where R$_0$ is the radical of a $C_1$–$C_{12}$alcohol, as of $C_1$–$C_{12}$alkanols, $C_5$–$C_8$cycloalkanols, phenol, ($C_1$–$C_6$alkyl)phenol, benzyl alcohol or ($C_1$–$C_6$alkyl)benzyl alcohol. A suitable inorganic ligand is $H_2O$. These ligands may preferably be $H_2O$ or organic compounds which can also be used as solvents in the inventive process and which are able to solvate the metal ions of the metal complexes. The organic ligands may contain one or more identical or different hetero atoms and hetero groups, in which case strongly co-ordinating compounds may also be encompassed, for example β-diketones (acetyl acetone), β-ketonates, (ethyl acetylacetate), β-dialdehydes (malonic dialdehyde), and β-ketoaldehydes (acetyl acetaldehyde).

Exemplary of such ligands are, in addition to water: alcohols of 1 to 12 carbon atoms (methanol, ethanol, n-propanol or isopropanol, n-butanol, isobutanol or ten-butanol, pentanol, hexanol, octanol, decanol, dodecanol, benzyl alcohol); nitriles and isonitriles (acetonitrile, propionitrile, butyronitrile, benzonitril, phenylacetonitrile and corresponding isonitriles); aldehydes (formaldehyde, acetaldehyde, propionaldehyde, benzaldehyde, pivaldehyde); ketones (acetone, methyl ethyl ketone, diethyl ketone, methyl isobutyl ketone), $C_1$–$C_4$alkyl esters of preferably aliphatic carboxylic acids (methyl, ethyl, propyl or butyl esters, preferably methyl esters, of formic, acetic, propionic or butyric acid, preferably of acetic acid); ethers (dimethyl ether, diethyl ether, dibutyl ether, ethylene glycol diethyl or dimethyl ether, tetrahydrofuran, dioxane); phosphites [(trifluormethyl)phosphites]. A preferred group of ligands comprises acetonitrile, benzonitrile, methanol, ethanol, phenol, acetone, pivaldehyde, ethyl acetate, diethyl ether, tetrahydrofuran, dioxane and water.

The metal complex salts can contain only the above mentioned weakly co-ordinating ligands, only strongly co-ordinating ligands or both types of ligand, the composition of the co-ordination number of the metal cation, which is preferably 2 to 8, more particularly 2 to 6 and, most preferably 2, 4 or 6, depending on the number of possible co-ordination points on the ligands and on the presence or absence of nucleophilic anions. Strongly co-ordinating ligands are preferably organic compounds which contain 2 to 30, preferably 2 to 20 and, most preferably, 2 to 26, carbon atoms, and contain, as complex forming groups, one or more identical or different, unsubstituted or substituted amino, phosphino, phosphonite, amino or stibino groups. Suitable substituents of these groups are $C_1$–$C_{12}$alkyl, preferably $C_1$–$C_6$alkyl, $C_5$cycloalkyl or $C_6$cycloalkyl, phenyl or benzyl, which are unsubstituted or substituted by $C_1$–$C_4$alkyl or $C_1$–$C_4$alkoxy. Some preferred examples of such groups are methyl, ethyl, cyclopentyl, cyclohexyl, methylcyclohexyl, phenyl, methylphenyl, methoxyphenyl, benzyl, methylbenzyl and methoxybenzyl. Particularly preferred groups are methyl, cyclohexyl, phenyl, methylphenyl and methoxyphenyl. The strongly co-ordinating ligands may be monodentate to tetradentate.

Exemplary of strongly co-ordinating monodentate ligands are in particular tertiary amines, phosphines, arsines and stibines, for example of formula $XR_1R_2R_3$, wherein X is N, P, As or Sb and $R_1$, $R_2$ and $R_3$ are each independently of one another $C_1$–$C_{12}$alkyl, preferably $C_1$–$C_6$alkyl, $C_5$cycloalkyl or $C_6$cycloalkyl, phenyl or benzyl, or $R_1$ and $R_2$, when taken together, are tetramethylene, pentamethylene or 3-oxa-1,5-pentylene, and $R_3$ is as previously defined, which radicals are unsubstituted or substituted by $C_1$–$C_4$alkyl or $C_1$–$C_4$alkoxy. Some preferred examples are methyl, ethyl, cyclopentyl, cyclohexyl, methylcyclohexyl, phenyl, methylphenyl, methoxyphenyl, benzyl, methylbenzyl and methoxybenzyl. Especially preferred groups are methyl, cyclohexyl, phenyl, methylphenyl and methoxyphenyl. $R_1$, $R_2$ and $R_3$ preferably have the same meaning. Exemplary of preferred amines, phosphines, arsines and stibines are trimethylamine, triethylamine, tri-n-propylamine, tri-n-butylamine, triphenylamine, tri(methylphenyl)amine, methyldiphenylamine and phenyldimethylamine, and the corresponding phosphines, arsines or stibines. The tertiary amines may also be pyridine or N-($C_1$–$C_6$alkylated) cyclic amines, typically N-methylmorpholine, N-methylpiperidine and N-methylpyrrolidine. Preferred monodentate ligands are the phosphines.

The complex forming groups in the strongly co-ordinating polydentate ligands may have the formula —$NR_1R_2$, —$PR_1R_2$, —$OPR_1R_2$, —$AsR_1R_2$ or —$SbR_1R_2$, the —$PR_1R_2$ group being preferred. $R_1$ and $R_2$ may each be independently of the other $C_1$–$C_{12}$alkyl, preferably $C_1$–$C_6$alkyl, $C_5$cycloalkyl or $C_6$cycloalkyl, phenyl or benzyl which are unsubstituted or substituted by $C_1$–$C_4$alkyl or $C_1$–$C_4$alkoxy. Some preferred examples are methyl, ethyl, cyclopentyl, cyclohexyl, methylcyclohexyl, phenyl, methylphenyl, methoxyphenyl, benzyl, methylbenzyl and methoxybenzyl. Methyl and phenyl are particularly preferred. Preferred complex forming groups are amino groups and, most preferably, phosphino groups. The polydentate ligands may contain identical or different complex forming groups of formula —$NR_1R_2$, —$PR_1R_2$, —$OPR_1R_2$, —$AsR_1R_2$ or —$SbR_1R_2$, typically —$NR_1R_2$ and —$PR_1R_2$, or —$PR_1R_2$ and —$OPR_1R_2$, or —$PR_1R_2$ and —$AsR_1R_2$.

The complex forming groups of the polydentate, preferably bidentate to tetradentate, ligands are preferably in the 1,2-, 1,3- or 1,4-positions of a carbon chain containing 2 to 4 carbon atoms. The complex forming groups of tri-and tetradentate ligands are preferably in the 1,2-, 1,3- or 1,4-positions of an aliphatic $C_2$–$C_4$carbon chain.

Exemplary of tridentate ligands are phosphines of formula $R_4C(CH_2PR_1R_2)_3$, wherein $R_1$ and $R_2$ are as previously defined, including the preferred meanings, and $R_4$ is H, $C_1$–$C_4$alkyl, phenyl or benzyl. Particularly preferred tridentate ligands are $CH_3$—$C[CH_2P(C_6H_5)_2]_3$ and bis[(2-diphenylphosphino)ethyl]phenylphosphine. Further examples of tridentate ligands are N,N',N''-pentaalkylated diethylenetriamines in which the alkyl groups preferably contain 1 to 4 carbon atoms. A typical example is N,N',N''-pentamethyldiethylenetriamine.

Exemplary of tetradentate ligands are $C[CH_2P(C_6H_5)]_4$, tris[(2-diphenylphosphino)ethyl]phosphine, tris[(2-dimethylamino)ethyl]amine and N,N',N'',N'''-hexamethyl-triethylenetetraamine.

A great number of bidentate ligands are known and described by H. Brunner in Topics in Stereochemistry, 18, pages 129–247, (1988). They may contain identical or different aforementioned complex forming groups and they may be aliphatic, cycloaliphatic, cycloheteroaliphatic, aromatic or heteroaromatic compounds containing preferably 2 to 30, most preferably 2 to 20, carbon atoms (without the carbon atoms in the complex forming groups), said complex forming groups in the aliphatic compounds being in 1,2-, 1,3- or 1,4-position and, in the cyclic compounds, in 1,2- or 1,3-position, and the hetero atoms being selected from the group consisting of O, S and N, and the number of hetero atoms being preferably 1 or 2, and the complex forming groups are attached direct or through a —$CR_5R_6$ group to the molecule, and $R_5$ and $R_6$ are each independently of the other H, $C_1$–$C_4$alkyl, phenyl or benzyl. Suitable complex forming groups are typically those of formula —$NR_1R_2$, —$PR_1R_2$, —$OPR_1R_2$, —$AsR_1R_2$ or —$SbR_1R_2$, the —$PR_1R_2$ group being preferred. $R_1$ and $R_2$ may each independently of the other preferably be $C_1$–$C_{12}$alkyl, more particularly $C_1$–$C_6$alkyl, $C_5$cycloalkyl or $C_6$cycloalkyl, phenyl or benzyl which are unsubstituted or substituted by $C_1$–$C_4$alkyl or $C_1$–$C_4$alkoxy. Some preferred examples are methyl, ethyl, cyclopentyl, cyclohexyl, methylcyclohexyl, phenyl, methylphenyl, methoxyphenyl, benzyl, methylbenzyl and methoxybenzyl. Methyl and phenyl are particularly preferred. Preferred complex forming groups are amino groups and, most preferably, phosphino groups. Further complex forming groups are in particular sp²-nitrogen atoms in unsaturated heterocyclic compounds, as for example in pyridines, oxazolines and pyrazoles, and two N-($C_1$–$C_6$alkylated), N-phenylated or N-benzylated imino groups which may be bound through a carbon chain containing 1 to 3 carbon atoms to the above molecules, or one such imino group attached conveniently to pyridines, oxazolines or pyrazoles.

In a preferred embodiment of the invention, the bidentate ligands may have formula I $$R_1R_2X—Y—X'R_1R_2 \qquad (I),$$

wherein X and X' are each independently of the other N, P, As, Sb or —OP, preferably P and —OP. X and X' are preferably identical. Most preferably X is P. $R_1$ and $R_2$ may each independently of the other be $C_1$–$C_{12}$alkyl, preferably $C_1$–$C_6$alkyl, $C_5$cycloalkyl or $C_6$cycloalkyl, phenyl or benzyl which are unsubstituted or substituted by $C_1$–$C_4$alkyl or $C_1$–$C_4$alkoxy. Y is a linear or branched alkylene or alkenylene radical of 2 to 20, preferably 2 to 12, carbon atoms, which radical is unsubstituted or substituted by $C_1$–$C_6$alkoxy, $C_5$cycloalkyl or $C_6$cycloalkyl, $C_5$cycloalkoxy or $C_6$cycloalkoxy, phenyl, phenoxy, benzyl or benzyloxy, and the cyclic substituents may be substituted by $C_1$–$C_6$alkyl or $C_1$–$C_6$alkoxy. The groups $R_1R_2X$— and $R_1R_2X'$— are in $\alpha,\beta$-, $\alpha$, $\gamma$-or $\alpha,\delta$-position, preferably in $\alpha,\beta$- or $\alpha\gamma$-position, in the alkylene or alkenylene radical.

Representative examples of compounds of formula I are: 1,2-diphenylphosphinoethane or 1,2-diphenylarsinoethane, 1,2-diphenylaminoethane, 1-diphenylamino-2-diphenylphosphinoethane, 1,2-or 1,3-diphenylphosphinopropane, 1,2-, 1,3-, 2,3-or 1,4-diphenylphosphinobutane, 1,2-di(p-methylphenyl)phosphinoethane, 1,2-di-(p-methoxyphenyl)phosphinoethane, 1,2-di-[(phenylmethyl)phosphino]ethane, 1,2-diphenylphosphino-1-phenylethane, 1,2-diphenyl-1,2-diphenylphosphinoethane, 1,2-, 1,3-, 1,4-, 2,3-, 3,4-, 2,4- or 2,5-diphenylphosphinohexane, 1,2-diphenylphosphonitoethane, 1,2-diphenylphosphinoethene, 1,2-or 1,3-diphenylphosphinopropene, 1,2-, 1,3-, 2,3- or 1,4-diphenylphosphinobut-1,2- or-2,3-ene.

In a further preferred embodiment of the invention, the bidentate ligands have the formula II

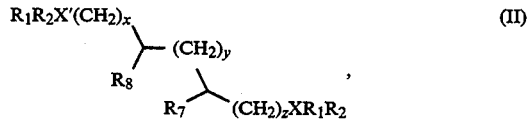

wherein X and X' are each independently of the other N, P, As, Sb or —OP, preferably P and —OP. X and X' are preferably identical. Most preferably X and X' are P. $R_1$ and $R_2$ may each independently of the other be $C_1$–$C_{12}$alkyl, preferably $C_1$–$C_6$alkyl, $C_5$cycloalkyl or $C_6$-cycloalkyl, phenyl or benzyl which are unsubstituted or substituted by $C_1$–$C_4$alkyl or $C_1$–$C_4$alkoxy. In formula II, x, y and z are each independently of one another 0 or 1, the sum of x+y+z being 0, 1 or 2, preferably 0 or 1. $R_7$ and $R_8$, together with the radical to which they are attached, form a 5- or 6-membered cycloaliphatic radical or a 5- or 6-membered cycloheteroaliphatic radical containing one or two identical or different hetero atoms selected from the group consisting of O, S and $NR_9$, which radicals are unsubstituted or substituted by $C_1$–$C_6$alkyl or $C_1$–$C_6$alkoxy or halogen, typically F, Cl and Br. $R_9$ is H, $C_1$–$C_6$alkyl, $C_1$–$C_8$acyl, phenyl or benzyl or phenyl or benzyl which are substituted by $C_1$–$C_6$alkyl or $C_1$–$C_6$alkoxy. If y is 0, $R_7$ and $R_8$, together with the radical to which they are attached, may form a 6-membered aromatic or heteroaromatic radical or a 5-membered heteroaromatic radical, which radicals are unsubstituted or substituted by $C_1$–$C_6$alkyl or $C_1$–$C_6$alkoxy or halogen, typically F, Cl and Br. The cycloaliphatic radicals or cycloheteroaliphatic radicals may be monocyclic or polycyclic, preferably bicyclic. The heteroaromatic radicals may contain O, S and N as hetero atoms.

Exemplary of substituents $R_7$ and $R_8$ for forming 5- or 6-membered cycloaliphatic rings which may be substituted as defined hereinabove are 1,2-ethylene, 1,2- or 1,3-propylene, 1-phenyl-1,2-ethylene, 2-phenyl-1,2-or 1,3-propylene, cyclopent-3,4-en-1,5-diyl, cyclopentan-1,5-diyl, cyclohexan-3,6-diyl, cyclohex-4,5-en-3,6-diyl, 1,4-butylene, 2-phenyl-1,4-butylene, 1,4-pentylene, 3-ethyl-1,4-butylene, 1-methylenephen-2-yl, 1,2-dimethylenebenzene.

Exemplary of substituents $R_7$ and $R_8$ for forming 5- or 6-membered cycloheteroaliphatic tings which may be substituted as defined hereinabove are —$CH_2O$—, —$CH_2OCH_2$—, —$OCH_2CH_2$—, —$CH_2OCH_2CH_2$—, —$CH_2OCH_2O$—, —$OCH_2CH_2O$—, —$OCR_{10}R_{11}O$—, wherein $R_{10}$ and $R_{11}$ are each independently of the other H, $C_1$–$C_6$alkyl, phenyl or benzyl or phenyl or benzyl which are substituted by $C_1$–$C_6$alkyl or $C_1$–$C_6$alkoxy, or are —$CH_2NR_9$—, —$CH_2NR_9CH_2$—, —$NR_9CH_2CH_2$—, —$CH_2R_9NCH_2CH_2$—, —$CH_2NR_9CH_2NR_9$—, —$NR_9CH_2CH_2NR_9$—, —$NR_9CH_2NR_9$—, wherein $R_9$ is H, $C_1$–$C_6$alkyl, $C_1$–$C_8$acyl, or phenyl or benzyl or phenyl or benzyl which are substituted by $C_1$–$C_6$alkyl or $C_1$–$C_6$alkoxy.

Exemplary of $R_9$ as alkyl are methyl, ethyl n- or isopropyl, n-butyl, isobutyl or tert-butyl, pentyl and hexyl; and $R_9$ as acyl may be formyl, acetyl, propionyl, butanoyl, benzoyl, methylbenzoyl, phenylacetyl, $C_1$–$C_6$alkoxy- or $C_5$cycloalkoxycarbonyl or $C_6$cycloalkoxycarbonyl or phenoxy- or benzyloxycarbonyl.

Exemplary of substituents $R_7$ and $R_8$ for forming 5- or 6-membered heteroaromatic rings or 6-membered aromatic rings which may be substituted as defined hereinabove are 1,2-phenylene, 2,3-naphthylene, pyrrol-3,4-diyl, furan-3,4-diyl, 2,3- or 3,4-pyridinediyl.

Representative examples of ligands of formula II are: 1,2-diphenylphosphinomethyl or 1,2-diphenylphosphinomethyl or 1-diphenylphosphino-2-diphenylphosphinomethyl- or 1-diphenylphosphino-3-diphenylphosphinocyclopentane,-cyclohexane,-benzene, or -indane; 2,3-diphenylphosphinonaphthalene, cyclohexane-1,2-bis(diphenylphosphonite), 1,2-bis(dimethylaminomethyl)cyclohexane, 1-dimethylaminomethyl-2-diphenylphosphinomethylcyclohexane, 1,2-diphenylphosphinonorbornane or -norbornene, 1,2-diphenylphosphino[2,2,2]bicyclooctane or-octene, 3,4-diphenylphosphino- or 3,4-diphenylphosphinomethyl or 3-diphenylphosphino-4-diphenylphosphinomethyl- or 2-diphenylphosphino-4-diphenylphosphino- or 2-diphenylphosphino-4-diphenylphosphinomethyltetrahydrofurane-tetrahydrothiophene or-pyrrolidine, or -N-methyl-, -N-butyl-, -N-benzyl-, -N-acetyl-, -N-benzoyl-, -N-phenoxycarbonyl- or -N-tert-butyloxycarbonylpyrrolidine, 2,3- or 3,4-diphenylphosphino- or 2,3- or 3,4-diphenylphosphinomethylpiperazine, 2,3-diphenylphosphino- or 2,3-diphenylphosphinomethylmorpholine or-dioxane, 4-methyl-or 4-phenyl-1,2-diphenylphosphino-or 1,2-diphenylphosphinomethyl or 1-diphenylphosphino-2-diphenylphosphinomethylcyclohexane, 4,5-diphenylphosphino- or 4,5-diphenylphosphinomethyl or 4-diphenylphosphino-5-diphenylphosphinomethyl-1,3-dioxolane or-2methyl, -2-butyl-, -2-phenyl-, -2-benzyl-, -2,2-dimethyl-, -2,2-diphenyl-, -2-methyl-2-phenyl- 1,3-dioxolane.

The bidentate ligands may also be biphenylene or naphthylene which are substituted in the o,o'-positions by identical or different groups —$XR_1R_2$, wherein the substituents X are each independently of one another N, P, As, Sb or —OP, preferably P and —OP. $R_1$ and $R_2$ may each independently of the other be $C_1$–$C_{12}$alkyl, preferably $C_1$–$C_6$alkyl, $C_5$cycloalkyl or $C_6$cycloalkyl, phenyl or benzyl which are unsubstituted or substituted by $C_1$–$C_4$alkyl or $C_1$–$C_4$alkoxy. The biphenyl or naphthyl may contain further substituents, typically $C_1$–$C_4$alkyl, $C_1$–$C_4$alkoxy, F or Cl. Representative examples of such ligands are 2,2'-diphenylphosphino- or 2,2'-bicyclohexylphosphinobiphenyl or -binaphthyl.

In a further embodiment of the invention, the bidentate ligands may also be ferrocenes of formulae III and IIIa

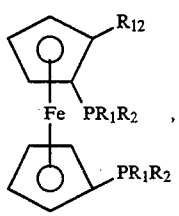
(III)

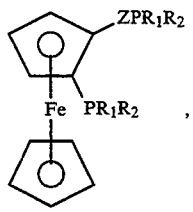
(IIIa)

wherein $R_1$ and $R_2$ are each independently of the other $C_1$–$C_{12}$alkyl, preferably $C_1$–$C_6$alkyl, $C_5$cycloalkyl or $C_6$cycloalkyl, phenyl or benzyl which are unsubstituted or substituted by $C_1$–$C_4$alkyl or $C_1$–$C_4$alkoxy, $R_{12}$ is H, $C_1$–$C_6$alkyl, $C_1$–$C_6$alkenyl, tri($C_1$–$C_6$alkyl)silyl, phenyl, benzyl, α-hydroxy- or α-[di($C_1$–$C_6$alkyl)amino]-$C_1$–$C_6$alkyl, and Z is methylene or $C_1$–$C_8$alkylidene. Exemplary of $R_{12}$ are H, methyl, ethyl, vinyl, allyl, trimethylsilyl, hydroxymethyl, 1-hydroxyeth-1-yl, aminomethyl and 1-dimethylaminoeth-1-yl. Z may be, in addition to methylene, ethylidene, 1,1- or 2,2-propylidene and benzylidene.

In another embodiment of the invention, the bidentate ligands may be α,α'-bipyridyl which is unsubstituted or substituted by $C_1$–$C_4$alkyl, $C_1$–$C_4$alkoxy, F or Cl.

In yet a further embodiment of the invention, the bidentate ligand may be pyridine which is substituted in α-position by $R_{13}$N=CH— or $R_{13}$N=CH—CH$_2$—, wherein $R_{13}$ is H, $C_1$–$C_6$alkyl, phenyl or benzyl. A typical example is α-(N-methyliminomethyl)pyridine.

Suitable bidentate ligands are also bisoxazolidines of formula IV,

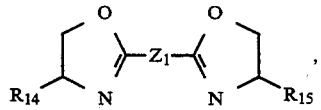
(IV)

wherein $R_{14}$ and $R_{15}$ are identical or different and are H, linear or branched $C_1$–$C_6$alkyl, phenyl, ($C_1$–$C_6$alkyl)-phenyl, benzyl or ($C_1$–$C_6$alkyl)benzyl, and $Z_1$ is a direct bond, methylene, $C_1$–$C_8$alkylidene, ethylene, 1,2-propylene or 1,2-phenylene. Examples of alkylidene have been cited previously.

Suitable bisoxazolidines are also those of formula V

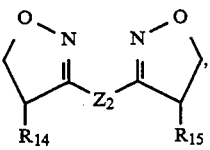
(V)

wherein $R_{14}$ and $R_{15}$ are identical or different and are H, linear or branched $C_1$–$C_6$alkyl, phenyl, ($C_1$–$C_6$alkyl)-phenyl, benzyl or ($C_1$–$C_6$alkyl)benzyl, and $Z_2$ is a direct bond, methylene, 1,2- or 1,3-phenylene, pyridine-2,6-diyl, ethylene, 1,2- or 1,3-propylene or 1,2-, 1,3-, 1,4- or 2,3-butylene or $C_2$–$C_8$alkylidene.

The metal complex salts can contain monodentate and/or polydentate ligands. Preferred combinations are two different strongly co-ordinating bidentate ligands, one bidentate strongly co-ordinating ligand and one monodentate strongly co-ordinating ligand, one bidentate strongly co-ordinating ligand and two monodentate weakly or strongly co-ordinating ligands, two different tridentate strongly co-ordinating ligands or one tridentate strongly co-ordinating ligand and three monodentate weakly or strongly co-ordinating ligands.

The polydentate ligands form with the metal cation 5- to 7-membered rings, preferably 5- and 6-membered rings.

The metal complex salts can contain nucelophilic (co-ordinating) anions. Exemplary of halide are in particular chloride, bromide and iodide. Exemplary of pseudohalide are cyanide and cyanate. The alcoholate can be linear or branched and contains preferably 1 to 4 carbon atoms. Representative examples are methylate, ethylate, n- or isopropylate and n-, iso- or tert-butylate. Exemplary of alkylphenolates are methyl-, ethyl-, n- or isopropyl, n-, iso- or tert-butyl-, dimethyl-, tert-butylmethyl- and di-tert-butylphenolate. Exemplary of secondary amido which preferably contain 2 to 8 atoms are dimethylamido, diethylamido, di-n-propyl- or diisopropylamido, di-n-butyl-, diisobutyl- or di-tert-butylamido, methylethylamido, dicyclohexylamido, pyrrolidin-N-ylamido, piperazin-N-ylamido and morpholin-N-ylamido. Exemplary of silylamido are bis(trimethylsilyl)- and bis(triethylsilyl)amido. Exemplary of alkyl-substituted cyclopentadienyl are methyl-, dimethyl-, pentamethyl-, ethyl-, propyl- and butylcyclopentadienyl. The halides are preferred, especially chloride, bromide and iodide.

The metal complex salts contain non-nucleophilic anions. The anions of oxyacids may typically be sulfate, phosphate, perchlorate, perbromate, periodate, antimonate, arsenate, nitrate, carbonate, the anion of a $C_1$–$C_8$carboxylic acid, for example formate, acetate, propionate, butyrate, benzoate, phenylacetate, mono-, di- or trichloroacetate or mono-, di- or trifluooracetate, sulfonate, typically methylsulfonate, ethylsulfonate, propylsulfonate, butylsulfonate, trifluormethylsulfonate (triflate), phenylsulfonate, benzylsulfonate, tosylate, mesylate or brosylate, and phosphonate for example methylphosphonate, ethylphosphonate, propylphosphonate, butylphosphonate, phenylphosphonate, p-methylphenylphosphonate and benzylphosphonate.

Preferred anions are tetrafluoroborate, hexafluorophosphate, perchlorate and triflate.

In a preferred embodiment of the novel process, the metal complex salts have the formula VI $$[(Q)_m(M^{+n})(S)_o(L^{-1})_q]^{+(n-q)}(A^{-r})_{(n-q)/r} \quad (VI),$$

wherein Q denotes identical or different strongly co-ordinating ligands, m is 0, or Q is a monodentate ligand and m is an integer from 1 to 8, Q is a bidentate ligand and m is an integer from 1 to 4, Q is a tridentate ligand and m is 1 or 2, or Q is a tetradentate ligand and m is 1 or 2, said monodentate, bidentate and tetradentate ligands containing one or more identical or different phosphino, phosphonito, arsino, or stibino groups or primary, secondary and/or tertiary amino groups and/or imino groups as complex forming groups, and said ligands form with the metal cation $M^{+n}$ a 5- to 7-membered, preferably a 5- or 6-membered ring; M is a metal selected from the second to the fifth main group, from the first to the eighth subgroup, or from the lanthanides, of the Periodic Table of the Elements, and n is an integer from 1 to 4; S is a weakly co-ordinating ligand selected from the group consisting of nitriles, aliphatic or aromatic alcohols, ketones, aldehydes, carboxylates, ethers, tris(trifluoromethyl)phosphite, and water, and o is 0 or an integer from 1 to 6; L is halide, pseudohalide, $C_1$-$C_8$alcoholate or unsubstituted or $C_1$-$C_4$alkyl-substituted phenolate, secondary amide of 2 to 12 carbon atoms, bis[(tri-$C_1$-$C_6$alkyl)silyl]amide or unsubstituted or $C_1$-$C_4$alkyl-substituted cyclopentadienyl, and q is 0 or an integer from 1 to 4; A is an anion of an oxyacid, $BF_4$, $PF_6$, $AsF_6$ or $SbF_6$, and r is an integer from 1 to 3, such that the the sum of (m×the number of possible co-ordination points on the ligand Q)+o+q is an integer from 2 to 8 and the sum of (m×the number of possible co-ordination points on the ligand Q)+o is at least 2.

For Q, M, S, L and A the same aforementioned preferences and exemplifications apply. In formula VI, r is preferably 1, q is preferably 0, 1 or 2, o is preferably 0, 1, 2 or 3, n is preferably 1, 2 or 3 and m is 0 or an integer from 1 to 6 and, most preferably, an integer from 1 to 4 in the case of monodentate ligands, an integer from 1 to 3, most preferably 1 or 2 in the case of bidentate ligands and, preferably 1 in the case of tridentate and tetradentate ligands. If m is 0, o is preferably an integer from 2 to 6. It is also preferred that M is a solvated cation, especially if m is 0 and the ligand S is simulataneously used as solvent in the novel process. Preferred combinations of ligands Q and S are: Q is a bidentate ligand, m is 1 or 2 and o is 2; Q is a tridentate ligand, m is 1 and o is 3.

The metal complex salts can be used in the novel process diect or prepared in situ before the reaction, especially if the ligand S is used simultaneously as solvent.

Suitable inert solvents are conveniently polar and, preferably, aprotic solvents which may be used singly or in mixtures of at least two solvents. Such solvents are typically: ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons(methylene chloride, chloroform, 1,2-dichloroethane, 1,1,1-trichloroethane, 1,1,2,2-tetrachloroethane), carboxylates and lactones (ethyl acetate, methyl propionate, ethyl benzoate, 2-methoxyethylacetate, γ-butyrolactone, δ-valerolactone, pivalolactone), carboxamides and lactams (N,N-dimethylformamide, N,N-diethylformamide, N,N-dimethylacetamide, tetramethylurea, hexamethylphosphoric triamide, γ-butyrolactam, ε-caprolactam, N-methylpyrrolidone, N-acetylpyrrolidone, N-methylcaprolactam), sulfoxides (dimethyl sulfoxide), sulfones (dimethyl sulfone, diethyl sulfone, trimethylenesulfone, tetramethylensulfone), tertiary amines (N-methylpiperidine, N-methylmorpholine), aromatic hydrocarbons such as benzene or substituted benzenes (chlorobenzene, o-dichlorobenzene, 1,2,4-trichlorobenzene, nitrobenzene, toluene, xylene) and nitriles (acetonitrile, propionitrile, benzonitrile, phenylacetonitrile).

Preferred solvents are halogenated aliphatic hydrocarbons, aromatic hydrocarbons, ethers and nitriles, for example methylene chloride, chloroform, benzene, toluene and acetonitrile.

The protected sugar and the aglycon are preferably used in equivalent amounts, but a small excess of the aglycon can also be used. If an orthoester is used concurrently, said ester is normally used in amounts of 1.2 to 10, preferably 1.2 to 5 and, most preferably, 1.5 to 3, equivalents per equivalent of protected sugar.

The reaction temperature may be in the range from −20° to +250° C., more particularly from 10° to 200° C. and, most preferably, from 20° to 150° C. A particularly preferred embodiment of the process comprises the concurrent use of an orthoester, the advantage being that the process can be carried out at room temperature.

The reaction time may be from minutes to days, mainly depending on the choice of catalyst, the type of reactants and the reaction conditions.

The manner in which the novel process is carried out may differ. It is expedient either to bind the water of reation chemically (e.g. with the aid of orthoesters) or to remove it continuously from the reaction mixture, conveniently by distillation or by addition of water absorbents such as silica gels or molecular sieves, or by addition of hydrophilic, at least partially dehydrated, inorganic salts such as $Na_2SO_4$, $MgSO_4$, $CaSO_4$, $MgCl_2$ or $CaCl_2$.

One process variant comprises charging the protected sugar and the catalyst in a solvent at room temperature to the reactor and then adding the aglycon and an orthoester. The mixture is then stirred at room temperature up to the reflux temperature of the solvent. A preferred embodiment of the process variant comprises the use of an orthoester of an alcohol which is simultaneously used as solvent.

Another process variant comprises charging the protected sugar and the aglycon in a solvent to the reasctor and then adding the catalyst, followed by the addition of a molecular sieve or, conveniently, magnesium sulfate. It is more advantageous to add the hydrophilic agent, for example the molecular sieve, in a soxhlet apparatus in a jacklet. The reaction mixture is then heated under reflux until the reaction is complete.

A further process variant comprises charging the protected sugar and the aglycon in a solvent to the reactor and then adding the catalyst, using an apparatus with water separator. The reaction mixture is then heated under reflux and the water of reaction is removed by distillation as an azeotrope until the reaction is complete.

The end of the reaction can be determined by spectroscopic or chromatographic methods. The desired reaction product is isolated by cooling the reaction mixture and separating the product by conventional separating methods such as distillation, extraction, crystallisation or chromatography.

Surprisingly, the novel process makes it possible to glycolise anomeric hydroxyl groups of protected sugars direct, the products being in addition obtained in very high yield and purity. Furthermore, the ratio of α- to β-form can be influenced, so that in individual cases even the one form or the other is obtained in virtually quantitative yield.

The inventive process is suitable for introducing protective groups into anomeric hydroxyl groups or for synthesising oligosaccharides, glycolipids and glycopeptides (q.v. for example H. Paulsen, Chem. Soc. Rev. 13, pages 15 to 45 (1984) und R. R. Schmidt, Angew. Chem. 98, pages 213 et seq. (1986). The process is also suitable for synthesising pharmaceutical drugs or agrochemicals, including natural substances such as pheromones or derivatives thereof, as described in the subsequent use Example.

The following Examples illustrate the invention in more detail.

A) WORKING EXAMPLES

Examples 1 to 24 (Orthoester process)

In a round flask, 1 equivalent of protected sugar (glycosyl donor) and 0.5 mol % of catalyst (Example 11: 5 mol %, Example 21: 0.15 mol %) are dissolved in 30 ml of methylene chloride and then 1 equivalent of aglycon (glycosyl acceptor) is added to the solution. The mixture is then stirred at room temperature (Examples 9, 11 and 12: 40° C.). The end of the reaction is determined by thin-layer chromatography (TLC plates, Merck, silica gel 60 F$_{254}$). To isolate the compounds, the reaction is concentrated by evaporation and the residue is chromatographed on silica gel 60 (granular size 0.04 to 0.063 mm). The ratio of α- to β-form is determined by $^1$H-NMR. Further particulars are given in Table 1.

The following catalysts are used:

A: [(1,1,1-tri(methylphenylphosphinomethyl)ethane)Rh(III)(NCCH$_3$)$_3$](CF$_3$CO$_2$)$_3$
B: [(1,2-diphenylphosphinoethane)Pd(II)(H$_2$O)$_2$](CF$_3$CO$_2$)$_2$
C: [(R(+)-2,2'-diphenylphosphinobinaphthyl)Pd(II)(H$_2$O)$_2$](CF$_3$CO$_2$)$_2$
D: [(S(−)-2,2'-diphenylphosphinobinaphthyl)Pd(II)(H$_2$)0$_2$](CF$_3$CO$_2$)$_2$
E: [(1,1,1-tri(phenylphosphinomethyl)ethane)Ru(II)(NCCH$_3$)$_3$](CF$_3$ CO$_2$)$_2$
F: [(1,1,1-tri(phenylphosphinomethyl)ethane)Rh(III)(NCCH$_3$)$_3$](CF$_3$CO$_2$)$_3$ The following protected sugars are used:

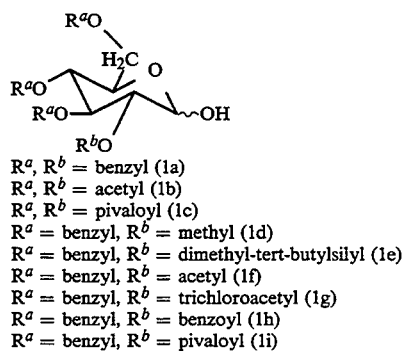

R$^a$, R$^b$ = benzyl (1a)
R$^a$, R$^b$ = acetyl (1b)
R$^a$, R$^b$ = pivaloyl (1c)
R$^a$ = benzyl, R$^b$ = methyl (1d)
R$^a$ = benzyl, R$^b$ = dimethyl-tert-butylsilyl (1e)
R$^a$ = benzyl, R$^b$ = acetyl (1f)
R$^a$ = benzyl, R$^b$ = trichloroacetyl (1g)
R$^a$ = benzyl, R$^b$ = benzoyl (1h)
R$^a$ = benzyl, R$^b$ = pivaloyl (1i)

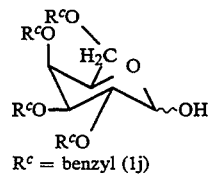

R$^c$ = benzyl (1j)

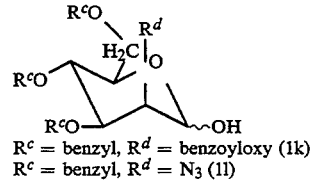

R$^c$ = benzyl, R$^d$ = benzoyloxy (1k)
R$^c$ = benzyl, R$^d$ = N$_3$ (1l)

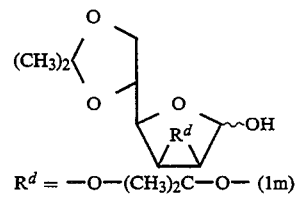

R$^d$ = —O—(CH$_3$)$_2$C—O— (1m)

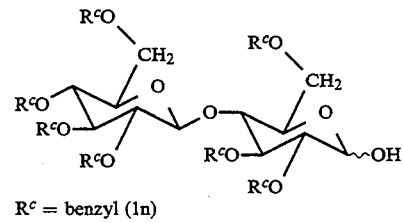

R$^c$ = benzyl (1n)

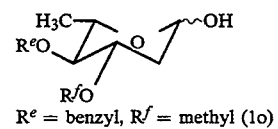

R$^e$ = benzyl, R$^f$ = methyl (1o)

TABLE 1

| Example | Sugar | Aglycon | Orthoester | Catalyst | Reaction-time (min.) | Yield (%) | Ratio of α:β-form |
|---|---|---|---|---|---|---|---|
| 1 | 1a | CH$_3$OH | HC(OCH$_3$)$_3$ | A | 300 | 91 | 47:51 |
| 2 | 1a | CH$_3$OH | HC(OCH$_3$)$_3$ | B | " | 91 | 50:50 |
| 3 | 1a | CH$_3$OH | HC(OCH$_3$)$_3$ | C | 240 | 88 | 53:47 |
| 4 | 1a | CH$_3$OH | HC(OCH$_3$)$_3$ | D | 240 | 88 | 50:50 |
| 5 | 1a | CH$_3$OH | HC(OCH$_3$)$_3$ | E | 6 days | 24 | 48:52 |
| 6 | 1a | CH$_3$OH | HC(OCH$_3$)$_3$ | F | 10 | 92 | 59:41 |
| 7 | 1a | C$_2$H$_5$OH | HC(C$_2$H$_5$O)$_3$ | F | 10 | 85 | 50:50 |
| 8 | 1a | allyl alcohol | HC(allyl-O)$_3$ | F | 5 | 96 | 62:38 |
| 9 | 1a | i-propanol | HC(i-propyl-O)$_3$ | F | 390 | 81 | 65:35 |
| 10 | 1a | phenol | HC(C$_6$H$_5$O)$_3$ | F | 10 | 72 | 37:63 |
| 11 | 1b | CH$_3$OH | HC(CH$_3$O)$_3$ | F | 48 hours | 52 | 11:89 |
| 12 | 1c | CH$_3$OH | HC(CH$_3$O)$_3$ | F | 18 hours | 60 | 4:96 |

TABLE 1-continued

| Example | Sugar | Aglycon | Orthoester | Catalyst | Reaction-time (min.) | Yield (%) | Ratio of α:β-form |
|---|---|---|---|---|---|---|---|
| 13 | 1d | CH₃OH | HC(CH₃O)₃ | F | 5 | 90 | 56:44 |
| 14 | 1e | CH₃OH | HC(CH₃O)₃ | F | 30 | 88 | 48:52 |
| 15 | 1f | CH₃OH | HC(CH₃O)₃ | F | 240 | 86 | 3:97 |
| 16 | 1g | CH₃OH | HC(CH₃O)₃ | F | 114 hours | 59 | 20:80 |
| 17 | 1h | CH₃OH | HC(CH₃O)₃ | F | 90 | 85 | 5:95 |
| 18 | 1i | CH₃OH | HC(CH₃O)₃ | F | 30 | 69 | 1:99 |
| 19 | 1j | CH₃OH | HC(CH₃O)₃ | F | 10 | 93 | 60:40 |
| 20 | 1k | CH₃OH | HC(CH₃O)₃ | F | 105 | 88 | 64:36 |
| 21 | 1l | phenol | HC(C₆H₅O)₃ | F | 150 | 89 | 97:3 |
| 22 | 1m | CH₃OH | HC(CH₃O)₃ | F | 1 | 65 | 99:1 |
| 23. | 1n | CH₃OH | HC(CH₃O)₃ | F | 120 | 93 | 60:40 |
| 24 | 1o | i-propanol | HC(i-propylO)₃ | F | 1 | 70 | 50:50 |

Examples 25–34, 35–39, 40–43, 44–56, 57–72, 73–85

The procedure of Example 1 is repeated, using tetra-O-benzyl-D-glucopyranose as protected sugar, methanol as aglycon and methyl orthoformate. The reaction is carded out at room temperature. The results are shown in Tables 2 to 7. Abbreviations: Ph=phenyl, Tf=triflate. The index n in the complex cations denotes solvated metal cations.

TABLE 2

| Example | Catalyst Complex cation | Anion | Solvent | Reaction time | Yield [%] | Ratio of α:β |
|---|---|---|---|---|---|---|
| 25 | 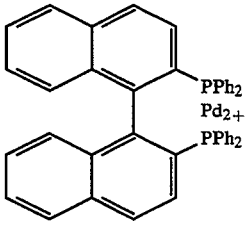 | ⁻OTf | CH₂Cl₂ | 12 h | 90 | 1:1.0 |
| 26 |  | ⁻PF₆ | CH₂Cl₂ | 12 h | 90 | 1:1.6 |
| 27 | 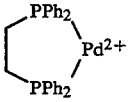 | ⁻OTf | CH₂Cl₂ | 12 h | 90 | 1:1.0 |
| 28 |  | ⁻PF₆ | CH₂Cl₂ | 12 h | 90 | 1:1.5 |
| 29 | 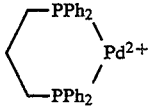 | ⁻PF₆ | CH₂Cl₂ | 48 h | 95 | 1:1.5 |
| 30 | 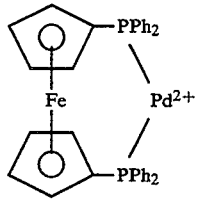 | ⁻OTf | CH₂Cl₂ | 10 min | 100 | 1:1.0 |
| 31 |  | ⁻PF₆ | CH₂Cl₂ | 2 h | 90 | 1:1.0 |
| 32 |  | ⁻BF₄ | CH₂Cl₂ | 12 h | 80 | 1:1.7 |
| 33 | 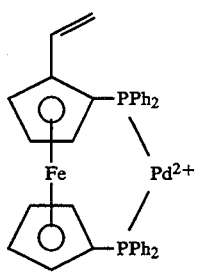 | ⁻OTf | CH₂Cl₂ | 30 min | 100 | 1:1.4 |

TABLE 2-continued
| Example | Catalyst Complex cation | Anion | Solvent | Reaction time | Yield [%] | Ratio of α:β |
|---|---|---|---|---|---|---|
| 34 | 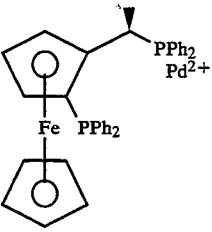 | ⁻OTf | $CH_2Cl_2$ | 12 h | 100 | 1:1.0 |
catalyst concentration: 5 mol %
TABLE 3
| Example | Catalyst Complex cation | Anion | Reaction time | Yield [%] | Ratio of α:β |
|---|---|---|---|---|---|
| 35 | 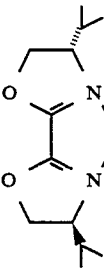 | ⁻OTf | 10 min | 100 | 2.0:1 |
| 36 | 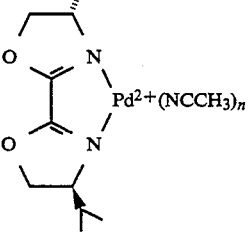 | ⁻BF₄ | 72 h | 60 | 1:2.0 |
| 37 | 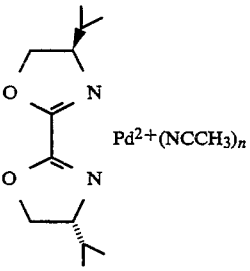 | ⁻OTf | 30 min | 100 | 1:1.0 |
| 38 | 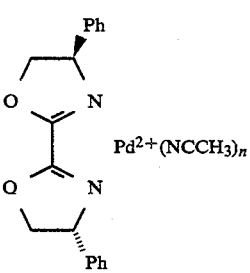 | ⁻OTf | 10 min | 100 | 1:1.0 |
| 39 | 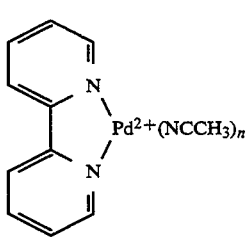 | ⁻OTf | 48 h | 70 | 1:1.0 |
Catalyst concentration: 5 mol %     Solvent: $CH_2CCl_2$

TABLE 4

| Example | Catalyst Complex cation | Anion | Reaction time | Yield [%] | Ratio of α:β |
|---|---|---|---|---|---|
| 40 | 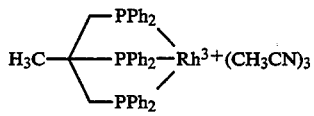 $H_3C-C(-PPh_2)(-PPh_2)(-PPh_2)-Rh^{3+}(CH_3CN)_3$ | $^-OTf$ | 5 min | 100 | 1.5:1 |
| 41 | $H_3C-C(-PPh_2)(-PPh_2)(-PPh_2)-Rh^{3+}(CH_3CN)_3$ | $^-BF_4$ | 12 h | 95 | 1:1.3 |
| 42 | $H_3C-C(-PPh_2)(-PPh_2)(-PPh_2)-Rh^{3+}(CH_3CH_2CH_2CN)_3$ | $^-OTf$ | 3 min | 100 | 1.5:1 |
| 43 | $H_3C-C(-PPh_2)(-PPh_2)(-PPh_2)-Rh^{3+}(PhCN)_3$ | $^-OTf$ | 1 min | 100 | 1.5:1 |

Catalyst concentration: 1 mol %     Solvent $CH_2Cl_2$

TABLE 5

| Example | Catalyst Complex cation | Anion | Solvent | Reaction time | Yield [%] | Ratio of α:β |
|---|---|---|---|---|---|---|
| 44 | $(C_6H_5CN)_n$-$Pt^{2+}$ | $^-OTf$ | $CH_2Cl_2$ | 12 h | 100 | 1:1.0 |
| 45 | $(C_6H_5CN)_n$-$Pt^{2+}$ | $^-BF_4$ | $CH_2Cl_2$ | 12 h | 60 | 1:3.0 |
| 46 | $(CH_3CN)_n$-$Cu^+$ | $^-OTf$ | $CH_2Cl_2$ | 20 min | 100 | 1:1.0 |
| 47 | $(CH_3CN)_n$-$Cu^+$ | $^-BF_4$ | $CH_2Cl_2$ | 72 h | 60 | 1:1.3 |
| 48 | $(CH_3CN)_n$-$Ce^{3+}$ | $^-OTf$ | $CH_2Cl_2$ | 1 h | 100 | 1:1.0 |
| 49 | $(CH_3CN)_n$-$Ce^{3+}$ | $^-OTf$ | $CH_2Cl_2/CH_3CN$ 10/3 | 12 h | 80 | 1:3.0 |
| 50 | $(CH_3CN)_n$-$Ce^{3+}$ | $^-BF_4$ | $CH_2Cl_2$ | 1 h | 95 | 1:1.6 |
| 51 | $(CH_3CN)_n$-$Ce^{3+}$ | $^-BF_4$ | $CH_2Cl_2/CH_3CN$ 10/3 | 12 h | 40 | 1:2.8 |
| 52 | $(CH_3CN)_n$-$Mg^{2+}$ | $^-OTf$ | $CH_2Cl_2$ | 12 h | 80 | 1:1.5 |
| 53 | $(CH_3CN)_n$-$Mg^{2+}$ | $^-OTf$ | $CH_2Cl_2/CH_3CN$ 10/3 | 12 h | 50 | 1:2.0 |
| 54 | $(CH_3CN)_n$-$Mg^{2+}$ | $^-BF_4$ | $CH_2Cl_2$ | 15 min | 100 | 1:1.7 |
| 55 | $(CH_3CN)_n$-$Mg^{2+}$ | $^-BF_4$ | $CH_2Cl_2/CH_3CN$ 10/3 | 12 h | 60 | 1:3.0 |
| 56 | $(H_2O)$-$Mg^{2+}$ | $^-ClO_4$ | $CH_2Cl_2$ | 72 h | 100 | 1:1.3 | catalyst concentration: 5 mol %

TABLE 6

| Example | Catalyst Complex cation | Anion | Solvent | Reaction time | Yield [%] | Ratio of α:β |
|---|---|---|---|---|---|---|
| 57 | $((CH_3CH_2)_2O_n)$-$Ag^+$ | $^-OTf$ | $CH_2Cl_2$ | 75 min | 90* | 1:1.4 |
| 58 | $((CH_3CH_2)_2O_n)$-$Ag^+$ | $^-BF_4$ | $CH_2Cl_2$ | 5 h | 55* | 1:1.4 |
| 59 | $((CH_3CH_2)_2O_n)$-$Ag^+$ | $^-PF_6$ | $CH_2Cl_2$ | 5 h | 55* | 1:1.4 |
| 60 | $(H_2O)$-$Ag^+$ | $^-ClO_4$ | $CH_2Cl_2$ | 5 h | 95* | 1:1.8 |
| 61 | $(CH_3CN)_n$-$Rh^{3+}$ | $^-OTf$ | $CH_2Cl_2$ | 5 min | 100 | 1:1.0 |
| 62 | $(CH_3CN)_n$-$Rh^{3+}$ | $^-OTf$ | $CH_2Cl_2/CH_3CN$ 10/3 | 12 h | 90 | 1:2.9 |
| 63 | $(CH_3CN)_n$-$Rh^{3+}$ | $^-BF_4$ | $CH_2Cl_2$ | 12 h | 80 | 1:1.2 |
| 64 | $(CH_3CN)_n$-$Rh^{3+}$ | $^-BF_4$ | $CH_2Cl_2/CH_3CN$ 10/3 | 12 h | 50 | 1:3.8 |
| 65 | $((CH_3CH_2)_2O)_n$-$Zn^{2+}$ | $^-OTf$ | $CH_2Cl_2$ | 10 min | 100 | 1:1.0 |
| 66 | $((CH_3CH_2)_2O)_n$-$Zn^{2+}$ | $^-OTf$ | $CH_2Cl_2/CH_3CN$ 10/3 | 12 h | 100 | 1:3.6 |
| 67 | $(CH_3CN)_n$-$Zn^{2+}$ | $^-BF_4$ | $CH_2Cl_2$ | 1 h | 100 | 1:1.9 |
| 68 | $(CH_3CN)_n$-$Zn^{2+}$ | $^-BF_4$ | $CH_2Cl_2/CH_3CN$ 10/3 | 12 h | 80 | 1:2.7 |
| 69 | $((CH_3CH_2)_2O)_n$-$Sn^{2+}$ | $^-OTf$ | $CH_2Cl_2$ | 1 min | 100 | 1:1.0 |
| 70 | $((CH_3CH_2)_2O)_n$-$Sn^{2+}$ | $^-OTf$ | $CH_2Cl_2/CH_3CN$ 10/3 | 12 h | 100 | 1:2.5 |
| 71 | $((CH_3CH_2)_2O)_n$-$B^{3+}$ | $^-F$ | $CH_2Cl_2$ | 90 min | 100 | 1:4.0 |
| 72 | $((CH_3CH_2)_2O)_n$-$B^{3+}$ | $^-F$ | $CH_2Cl_2CH_3CN$ | 4 h | 60 | 1:14.0 |

TABLE 6-continued

| Ex-ample | Catalyst Complex cation | Anion | Solvent | Reaction time | Yield [%] | Ratio of α:β |
|---|---|---|---|---|---|---|
| | | | 10/3 | (−20° C.) | | |

Catalyst concentration: 5 mol %
*reaction solutions are heterogeneous

TABLE 7

| Ex-ample | Catalyst Complex cation | Anion | Solvent | Reaction time | Yield [%] | Ratio of α:β |
|---|---|---|---|---|---|---|
| 73 | $(CH_3CN)_n\text{-}Pd^{2+}$ | $^-OTf$ | $CH_2Cl_2$ | 10 min | 100 | 1:1.0 |
| 74 | $(CH_3CN)_n\text{-}Pd^{2+}$ | $^-PF_6$ | $CH_2Cl_2$ | 12 h | 100 | 1:1.3 |
| 75 | $(CH_3CN)_n\text{-}Pd^{2+}$ | $^-BF_4$ | $CH_2Cl_2$ | 12 h | 60* | 1:1.3 |
| 76 | $(CH_3CN)_n\text{-}Pd^{2+}$ | $^-BF_4$ | $CH_3CN$ | 12 h | 95 | 1:4.0 |
| 77 | $(CH_3CN)_n\text{-}Pd^{2+}$ | $^-BF_4$ | $CH_2Cl_2/CH_3NO_2$ 10/3 | 10 min | 100 | 1:1.2 |
| 78 | $(CH_3CN)_n\text{-}Pd^{2+}$ | $^-BF_4$ | $CH_2Cl_2/CH_3CN$ 10/1 | 20 h | 100 | 1:3.1 |
| 79 | $(CH_3CN)_n\text{-}Pd^{2+}$ | $^-BF_4$ | $CH_2Cl_2/CH_3CN$ 10/2 | 20 h | 100 | 1:4.2 |
| 80 | $(CH_3CN)_n\text{-}Pd^{2+}$ | $^-BF_4$ | $CH_2Cl_2/CH_3CN$ 10/3 | 20 h | 100 | 1:5.4 |
| 81 | $(CH_3CN)_n\text{-}Pd^{2+}$ | $^-BF_4$ | $CH_2Cl_2/CH_3CN$ 10/6 | 20 h | 80 | 1:5.0 |
| 82 | $(CH_3CN)_n\text{-}Pd^{2+}$ | $^-BF_4$ | $CH_2Cl_2/CH_3CN$ 10/10 | 20 h | 70 | 1:4.0 |
| 83 | $(CH_3CN)_n\text{-}Pd^{2+}$ | $^-BF_4$ | $CH_2Cl_2/CH_3CN$ 10/3 | 72 h | 70 | 1:4.0 |
| 84 | $(CH_3CN)_n\text{-}Pd^{2+}$ | $^-BF_4$ | $CH_2Cl_2/CH_3CN$ 10/10 | 72 h | 70 | 1:5.6 |
| 85 | $(CH_3CN)_n\text{-}Pd^{2+}$ | $^-OTf$ | $CH_2Cl_2/CH_3CN$ 10/3 | 12 h | 100 | 1:2.5 |

Catalyst concentration: 5 mol %
Example 83: i-propanol/triisopropanol formate
Example 84: allyl alcohol $(CH_2=CHCH_2O_3)CH$
*reaction solution is heterogeneous!

Examples 86–103 (Soxhlet Process)

In a 50 ml flask with a soxhlet, containing a jacket filled with an activated molecular sieve (4 Angstrom), are placed 1 equivalent of the protected sugar (q.v. Example 1) and 1 equivalent of the aglycon in 30 ml of methylene chloride. The reaction mixture is heated to reflux temperature (40° C.) and reacted at this temperature. After cooling the reaction mixture, the solvent is removed by evaporation and the residue is chromatographed as described in Example 1. Further particulars are given in Table 8.

The following aglycons are used:

benzyl alcohol (2a), p-methoxyphenol (2b), 8-(p-methoxyphenoxy)octan-1-ol (2c), cholesterol (2d), 3,7-dimethyl-oct-6-en-1-ol (2e), 1-(p-methoxyphenoxy)-7-benzoyloxytetradecan-14-ol (2f), 2-azido-dodecan-1-ol (2g), 2-azido-3-benzyloxy-oct-4-en-1-ol (2h), and protected sugars of formula

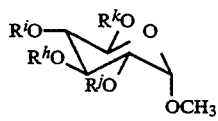

2i: $R^h$, $R^i$ and $R^j$ = benzyl, $R^k$ = hydrogen
2j: $R^h$, $R^i$ and $R^k$ = benzyl, $R^j$ = hydrogen
2k: $R^h$, $R^j$ and $R^k$ = benzyl, $R^i$ = hydrogen

TABLE 8

| Ex-ample | Sugar | Aglycon | Reaction time (hours) | Yield (%) | Ratio of α:β |
|---|---|---|---|---|---|
| 86 | 1a | 2a | 23 | 87 | 64:36 |
| 87 | 1a | 2b | 23 | 64 | 64:36 |
| 88 | 1a | 2c | 20 | 94 | 59:41 |
| 89 | 1a | 2d | 17 | 67 | 66:34 |
| 90 | 1a | 2e | 40 | 88 | 64:36 |
| 91 | 1a | 2i | 27 | 81 | 74:26 |
| 92 | 1h | 2c | 16 | 96 | β-form |
| 93 | 1h | 2f | 24 | 95 | β-form |
| 94 | 1h | 2i | 15,5 | 75 | β-form |
| 95 | 1f | 2c | 19 | 71 | β-form |
| 96 | 1f | 2i | 21,5 | 56 | β-form |
| 97 | 1j | 2c | 21,5 | 71 | 60:40 |
| 98 | 1k | 2c | 260 | 20 | 60:40 |
| 99 | 1n | 2c | 20 | 46 | 50:50 |
| 100 | 1h | 2j | 20 | 78 | β-form |
| 101 | 1h | 2k | 48 | 27 | β-form |
| 102 | 1h | 2g | 24 | 90 | β-form |
| 103 | 1h | 2h | 24 | 43 | β-form |

Examples 104–108 (Water separation process)

In a 50 ml round flask fitted with water separator, 1 equivalent of the protected sugar and 1 equivalent of the aglycon are dissolved in 25 ml of benezene (Example 105: $CH_2Cl_2$) and 0.5 mol % of catalyst F is added. The mixture is then heated to reflux (80° C.) (Example 105: 40° C.) and stirred at this temperature. To isolate the reaction products, the solvent is removed by distillation and the residue is chromatographed as described in Example 1. Further particulars are given in Table 9.

TABLE 9

| Example | Sugar | Aglycon | Reaction time (hours) | Yield (%) | Ratio of α:β |
|---|---|---|---|---|---|
| 104 | 1a | 2l | 40 | 50 | 65:35 |
| 105 | 1a | 2m | 22 | 30 | 64:36 |

TABLE 9-continued

| Example | Sugar | Aglycon | Reaction time (hours) | Yield (%) | Ratio of α:β |
|---|---|---|---|---|---|
| 106 | 1a | 2c | 44 | 69 | 50:50 |
| 107 | 1i | 2c | 134 | 72 | 30:70 |
| 108 | 1n | 2i | 38 | 41 | 60:40 |

2l = 1-(p-methoxyphenyloxy)-5-hydroxyhexane

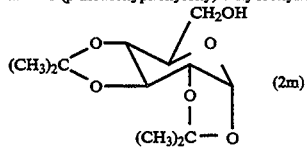

(2m)

Examples 109–111: Use of dehydrating reagents

In a 50 ml round flask, 1 equivalent of the protected sugar and 1 equivalent of the aglycon are dissolved in 25 ml of $CH_2C_2$. Then 1 g of $MgSO_4$ is added, followed by the addition of 3 mol % of $Fe(ClO_4)_3$ as catalyst. The mixture is then heated to reflux and stirred for 1 hour at this temperature. To isolate the reaction products, the solvent is removed by distillation and the residue is chromatographed as described in Example 1. Further particulars are given in Table 10.

TABLE 10

| Example | Sugar | Aglycon | Yield (%) | Ratio of α:β |
|---|---|---|---|---|
| 109 | 1a | 2c | 95 | 62:38 |
| 110 | 1a | 2n | 76 | 50:50 |
| 111 | 1h | 2c | 94 | β-form |

2n = cyclohexanol

B) Use Examples: Synthesis of compounds which inhibit oviposition in cherry flies (compound 13)

Example B1

To 16.42 g (94.36 mmol) of (1) in 180 ml dimethyl formamide (DMF) are added 14.95 g (99.1 mmol) of tert-butyldimethylchlorosilane and 13.49 g (198.2 mmol) of imidazole at room temperature (RT) and the reaction mixture is stirred overnight at RT. Afterwards the reaction mixture is taken up in 300 ml of $CH_2Cl_2$, washed once with water and once with concentrated aqueous NaCl (brine) and then dried over $Na_2SO_4$. The solvent is stripped off on a rotary evaporator (ROT) and the residue (27.4 g) is used without further purification in Example B2. Abbreviations: Et=ethyl, Me=-methyl, Bu=butyl, Bn=benzyl, Bz=benzoyl.

Example B2

The residue obtained in Example B1 is dissolved in 60 ml of diethyl ether (ether) and the solution is added dropwise over 30 minutes to a solution of 3.59 g (94.36 mmol) of $LiAlH_4$ in 150 ml of ether. To the reaction mixture are then added at 0° C., in succession, 10.8 ml of $H_2O$, 10.8 ml of NaOH and 32.4 ml of $H_2O$. The batch is stirred for 10 minutes, filtered over diatomaceous earth and the filtrate is dried over $MgSO_4$. The solvent is stripped off on a ROT and the residue is chromatographed on silica gel (hexane/ether/3:1). Yield: 20.94 g (3); $^1$H-NMR (250 MHz, $CDCl_3$): 3.55 (t, J=7, —$CH_2$—OSi).

Example B3

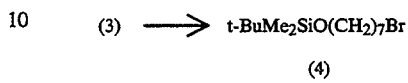

2.4 ml of 1-bromo-2-N,N-trimethylpropenylamine are added dropwise over 20 minutes at RT to 3.76 g (15.25 mmol) of (3) in 24 ml of benzene. The reaction mixture is then stirred for 20 minutes at RT and the solvent is subsequently stripped off on a ROT and the residue is chromatographed on silica gel (hexane/ether/19:1). Yield: 4.53 g of (4); $^1$H-NMR (250 MHz, $CDCl_3$): 3.55 (t, J=7, —$CH_2Br$).

Example 4

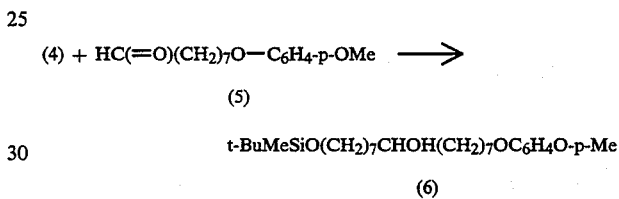

4.46 g (14.41 mmol) of (4) in 15 ml of tetrahydrofuran (THF) are reacted at RT with 350 mg of magnesium. After cooling the reaction mixture, 3.61 g (14.41 mmol) of (5) in 10 ml of THF are added dropwise while cooling with ice. The reaction mixture is allowed to warm to room temperature and stirred for 1 hour. Then 15 ml of 2N $H_2SO_4$ and 50 ml of ether are added and the organic phase is separated, washed with water and brine, dried over $Na_2SO_4$ and the solvent is stripped off on a ROT. The residue is chromatographed on silica gel (pentane/ethyl acetate 8:1). Yield: 5.82 g of (6); $^1$H-NMR (250 MHz, $CDCl_3$): 3.90 (t, J=7, —$CH_2O$—).

Example 5

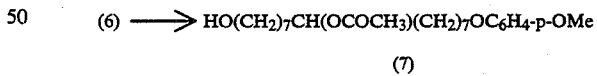

2.51 g (5.24 mmol) of (6), 1.7 ml of acetic anhydride and 2.8 ml of pyridine dissolved in 5 ml of $CH_2Cl_2$ are stirred overnight at RT. The reaction mixture is then diluted with ethyl acetate, washed once with each of 1N HCl, $H_2O$, saturated aqueous $NaHCO_3$ and brine and then dried over $Na_2SO_4$. The solvent is then stripped off on a ROT, and the residue is dissolved in THF. Then (n-butyl)$_4$NF is added and the mixture is stirred for 3 hours at RT. After dilution with $CH_2Cl_2$, washing 3 times with $H_2O$, drying over $Na_2SO_4$ and removing the solvent on a ROT, the residue (2.1 g) is used without further purification in Example 6.

$^1$H-NMR (500 MHz, $CDCl_3$): 3.88 (t, J=7, —$CH_2O$—), 3.74 (s, —$OCH_3$).

Example B6

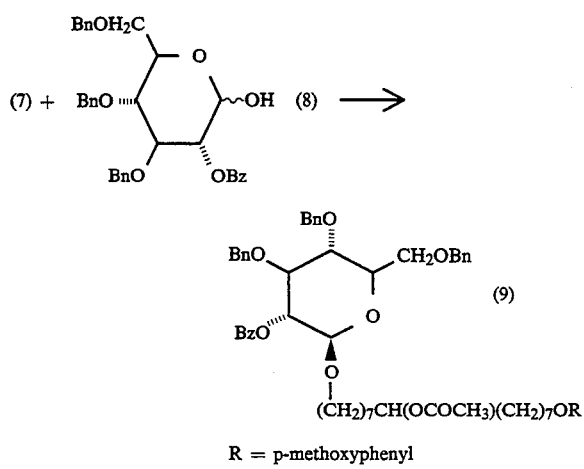

R = p-methoxyphenyl

A solution of 1.5 g (2.7 mmol) of (8), 1.23 g (2.7 mmol) of (7) and 5 mg of (0.14 mol %) of catalyst F in 60 ml of $CH_2Cl_2$ is refluxed for 24 hours in a round flask equipped with a Soxhlet apparatus (jacket with 4 angström molecular sieve). The solvent is afterwards removed on a ROT and the residue is chromatographed on silica gel (petroleum ether (40/60)/ethyl acetate/8:1). Yield: 2.34 g (92%) of (9); $^{13}C$-NMR (500 MHz, $CDCl_3$): 101.2 (d, C(1)).

Example B7

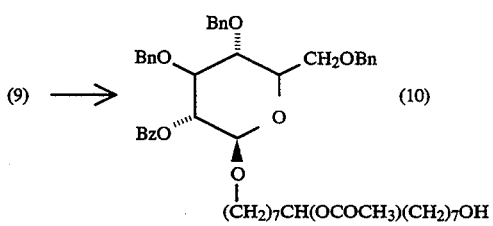

2.08 g (2.2 mmol) of (9) and 4.4 g of cerammonium nitrate are dissolved in 30 ml of acetonitrile. After addition of 7.5 ml of $H_2O$, the reaction mixture is stirred at 0° C. for 10 minutes, then diluted with ether, washed once with each of $H_2O$, saturated aqueous $NaHCO_3$ and brine. The separated organic phase is dried over $Na_2SO_4$. The solvent is distilled off on a ROT and the residue is chromatographed on silica gel (petroleum ether (40/60)/ethyl acetate/2:1). Yield: 1.6 g of (10); $^1H$-NMR (300 MHz, $CDCl_3$): 4.51 (d, J=8, anomeric H).

Example B8

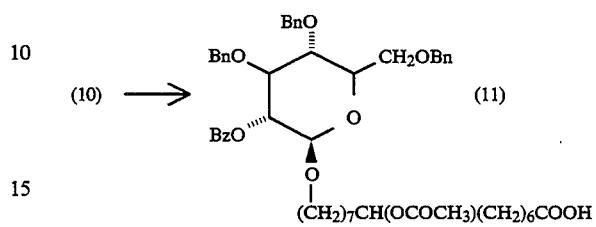

1.54 g (1.84 mmol) of (10) are dissolved in 20 ml of acetone and to the solution is added at 0° C. a 4N solution of $CrO_3/H_2SO_4$ (1:1) in acetone. The reaction mixture is then stirred for 30 minutes at 0° C., diluted with ether, filtered through cotton wool, and the filtrate is washed once with $H_2O$ and once with brine. After drying over $Na_2SO_4$, the solvent is distilled off on a ROT and the residue is chromatographed on silica gel (petroleum ether (40/60)/ethyl acetate/75:22:3). Yield: 1.18 g of (11); $^1H$-NMR (300 MHz, $CDCl_3$): 4.61 (d, J=8, anomeric H).

Example B9

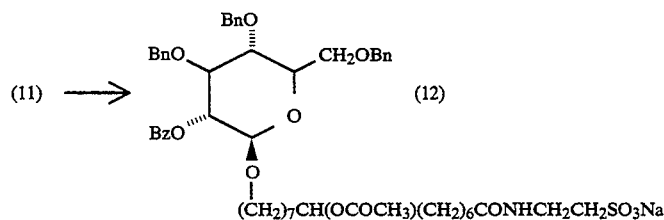

A mixture of 1.28 g (1.50 mmol) of (11), 207 mg of N-hydroxysuccinimide and 402 mg of dicyclohexylcarbodiimide in 10 ml of dimethoxyethane is stirred at room temperature for 17 hours. The reaction mixture is then filtered, the filter product is washed with 10 ml of dimethoxyethane, and the filtrate is concentrated. The residue is dissolved in 12 ml of methanol and to the solution are added at RT 188 mg of taurin in 1.58 ml of 1N NaOH and 4 ml of methanol. The mixture is stirred for 1.5 hours at RT, then concentrated, and the residue is chromatographed on silica gel (chloroform/methanol/4:1). Yield: 1.18 g of (12); $^1H$-NMR (300 MHz, $CDCl_3$): 4.46 (d, J=8, anomeric H).

Example B 10

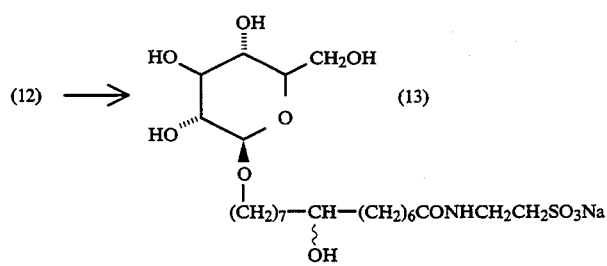

1.26 g (1.28 mmol) of (12) in 10 ml of methanol and a catalytic amount of Na are stirred for 3 hours at RT. The reaction mixture is then concentrated and filtered over silica gel. The solvent is removed on a ROT and the residue is dissolved in methanol and hydrogenated with Pd/C (5%) in a $H_2$ atmosphere for 8 hours. The mixture is then filtered over Celite, the solvent is removed on a ROT, and the crude product is chromatographed on reverse phase silica gel $C_{18}$ with acetonitrile/$H_2O$. Yield: 628 mg of (13); $^1$H-NMR (500 MHz, $CD_3OD$): 3.89 (dt, $J_1=9$, $J_2=7$, C—O—$HC_2$), 3.59 (t, J=7, S—$CH_2$), 3.53 (dt, $J_1=9,5$, $J_2=7$, C—O—$CH_2$), 3.50 (m, HC—OH), 2.96 (t, J=7, $NCH_2$), 2.19 (t, J=7,4, —C(O)—$CH_2$).

What is claimed is:

1. A process for preparing a glycoside, which process comprises reacting, in an inert solvent, an anomeric hydroxyl group containing protected sugar with an aglycon, alone or together with an orthoester, in the presence of a catalytic amount of a metal complex salt, wherein the anomeric hydroxyl group containing protected sugar is a protected monosaccharide having an anomeric hydroxyl group, or a derivative thereof, or a protected oligosaccharide having an anomeric hydroxyl group, or a derivative thereof; the aglycon is selected from the group consisting of an aliphatic alcohol, a cycloaliphatic alcohol, an aromatic alcohol, an aromatic-aliphatic alcohol, a non-anomeric hydroxyl group containing protected monosaccharide, or a derivative thereof, and a non-anomeric hydroxyl group containing protected oligosaccharide, or a derivative thereof; and wherein the metal complex salt comprises a metal cation, a ligand which is a monodentate ligand or a polydentate ligand and a non-nucleophilic anion, wherein the metal cation is a cation of a lanthanide metal or a metal selected from the group consisting of Mg, Ca, Sr, Ba, B, Al, Ga, In, Sn, Pb, Sb, Bi, Cu, Ag, Au, Zn, Cd, Hg, Sc, Y, Ti, Zr, Hf, V, Nb, Ta, Cr, Mo, W, Mn, Fe, Co, Ni, Ru, Rh, Pd, Os, Ir and Pt, and the non-nucleophilic anion is an anion of an oxyacid, $BF_4$, $PF_6$, $AsF_6$ or $SbF_6$.

2. A process according to claim 1, wherein the process is carried out in the presence of a orthoester at room temperature.

3. A process according to claim 1, wherein the anomeric hydroxyl group containing protected mono- and oligosaccharides are aldoses or ketoses which carry an anomeric hydroxyl group.

4. A process according to claim 3, wherein the anomeric hydroxyl group containing protected monosaccharides are selected from the group consisting of aldopyranoses, aldofuranoses, ketopyranoses and ketofuranoses which carry an anomeric hydroxyl group.

5. A process according to claim 1, wherein the anomeric hydroxyl group containing protected mono- and oligosaccharide derivatives are protected deoxy sugars, amino sugars, thiosugars, sugar acids or esters of sugar acids which carry an anomeric hydroxyl group.

6. A process according to claim 1, wherein the orthoester is derived from a $C_1$-$C_4$carboxylic acid.

7. A process according to claim 6, wherein the orthoesters are derived from formic acid, acetic acid, propionic acid or butyric acid.

8. A process according to claim 7, wherein the orthoesters are derived from formic acid.

9. A process according to claim 6, wherein the orthoester is derived from a $C_1$-$C_4$carboxylic acid and a linear or branched $C_1$-$C_{20}$alkanol, a $C_2$-$C_{20}$alkenol carrying a non-vinylic alcohol group, a mono- or polycycloaliphatic or a mono- or polycycloheteroaliphatic $C_3$-$C_{20}$alcohol containing the hetero atoms O, S and N, an aromatic $C_6$-$C_{20}$alcohol, or an aromatic-aliphatic $C_7$-$C_{20}$alcohol which is unsubstituted or substituted by $C_1$-$C_6$alkyl, $C_1$-$C_6$alkoxy or $C_1$-$C_6$alkylthio, phenoxy $C_1$-$C_4$alkylphenoxy or $C_1$-$C_4$alkoxyphenoxy, benzyl, benzyloxy or $C_1$-$C_4$alkylbenzyloxy or $C_1$-$C_4$alkoxybenzyloxy.

10. A process according to claim 9, wherein the orthoester is an ester of a $C_1$-$C_4$alkanol, allyl alcohol, benzyl alcohol or phenol.

11. A process according to claim 1, wherein the aglycons are protected sugars or sugar derivatives the anomeric hydroxyl group of which is protected and which contain a free hydroxyl group.

12. A process according to claim 11, wherein the sugars or sugar derivatives carry a free hydroxymethyl group.

13. A process according to claim 1, wherein the metal complex salts are used in an amount of 0.01 to 20 mol %, based on the amount of the sugar or sugar derivative.

14. A process according to claim 1, wherein the metal complex salts are used in an amount of 0.01 to 10 mol %, based on the amount of the sugar or sugar derivative.

15. A process according to claim 1 wherein the metal complex salt further comprises a nucleophilic anion selected from the group consisting of halide, pseudohalide, $C_1$-$C_8$alcoholate, unsubstituted or $C_1$-$C_4$substituted phenolate, secondary amido containing 2 to 12 carbon atoms, bis((tri-$C_1$-$C_6$alkyl)silyl)amido and unsubstituted or $C_1$-$C_4$alkyl substituted cyclopentadienyl anions.

16. A process according to claim 1, wherein the metal cations are derived from the following metals: Mg, Ca, B, In, Sn, Pb, Cu, Ag, Au, Zn, Ti, Zr, V, Cr, Mo, W, Mn, Fe, Co, Ni, Ru, Rh, Pd, In, Pt, Ce, Nd and Yb.

17. A process according to claim 1, wherein the ligand is non-chiral or chiral.

18. A process according to claim 1, wherein the ligand is monodentate to tridentate.

19. A process according to claim 1, wherein the polydentate and the metal cation form a 5- to 7-membered ring.

20. A process according to claim 1, wherein the polydentate ligand has complex forming groups in the 1,2-, 1,3- or 1,4-positions of a carbon chain containing 2 to 4 carbon atoms.

21. A process according to claim 1, wherein the ligands are weakly co-ordinating organic ligands which contain 1 to 20 carbon atoms, and which contain hetero atoms or hetero groups capable of co-ordination, or are $H_2O$.

22. A process according to claim 21, wherein the hetero atoms or hereto groups are —OH, —CN, —CHO, —CO—, —O—, —C(O)$OR_0$ and P(O—)$_3$, where $R_0$ is the radical of a $C_1$-$C_{12}$alcohol.

23. A process according to claim 21, wherein the weakly co-ordinating ligands are selected from the group consisting of alcohols of 1 to 12 carbon atoms, nitriles, isonitriles, aldehydes, ketones, $C_1$-$C_4$alkyl esters of aliphatic carboxylic acids, ethers or phosphites.

24. A process according to claim 23, wherein the weakly co-ordinating ligands are selected from the group consisting of acetonitrile, benzonitrile, methanol, ethanol, phenol, acetone, pivaldehyde, ethyl acetate, diethyl ether, tetrahydrofuran, dioxane and water.

25. A process according to claim 1, wherein the metal complex salts contain only weakly co-ordinating ligands, only strongly co-ordinating ligands or both types of ligand.

26. A process according to claim 25, wherein the strongly co-ordinating ligands are organic compounds which contain 2 to 30 carbon atoms, and, as complex forming groups, contain one or more identical or different, unsubstituted or substituted amino, phosphino, phosphonite, arsino or stibino groups.

27. A process according to claim 26, wherein the amino, phosphino, phosphonite, arsino or stibino groups are substituted by $C_1$-$C_{12}$alkyl, $C_5$cycloalkyl or $C_6$cycloalkyl, phenyl or benzyl which are in turn unsubstituted or substituted by $C_1$-$C_4$alkyl or $C_1$-$C_4$alkoxy.

28. A process according to claim 26, wherein the ligand is monodentate and the strongly co-ordinating groups are tertiary amines, phosphines, arsines or stibines.

29. A process according to claim 28, wherein the monodentate strongly co-ordinating ligands are those of formula $XR_1R_2R_3$, wherein X is N, P, As or Sb and $R_1$, $R_2$ and $R_3$ are each independently of one another $C_1$ - $C_{12}$ alkyl, $C_5$cycloalkyl or $C_6$cycloalkyl, phenyl or benzyl, or $R_1$ and $R_2$, when taken together, are tetramethylene, pentamethylene or 3-oxa-1,5-pentylene, and $R_3$ is as previously defined, which are unsubstituted or substituted by $C_1$-$C_4$alkyl or $C_1$-$C_4$alkoxy.

30. A process according to claim 28, wherein the monodentate strongly co-ordinating ligands are tertiary phosphines.

31. A process according to claim 1, wherein the polydentate ligands have complex forming groups of the formula $-NR_1R_2$, $-PR_1R_2$, $-OPR_1R_2$, $-AsR_{12}$ or $-SbR_1R_2$, wherein $R_1$ and $R_2$ are each independently of the other $C_1$-$C_{12}$alkyl, $C_5$cycloalkyl or $C_6$cycloalkyl, phenyl or benzyl which are unsubstituted or substituted by $C_1$-$C_4$alkyl or $C_1$-$C_4$alkoxy.

32. A process according to claim 31, wherein the complex forming group has the formula $-PR_1R_2$.

33. A process according to claim 31, wherein the ligands are phosphines of formula $R_4C(CH_2PR_1R_2)_3$, wherein $R_1$ and $R_2$ are as defined in claim 31, and $R_4$ is H, $C_1$-$C_4$alkyl, phenyl or benzyl, or N,N',N'''-pentaalkylated diethylenetriamines in which the alkyl groups contain 1 to 4 carbon atoms.

34. A process according to claim 33, wherein the ligands are $CH_3-C[CH_2P(C_6H_5)]_3$, bis[(2-diphenylphosphino)ethyl]phenylphosphine, or N, N',N''-pentamethyldiethylenetriamine.

35. A process according to claim 1, wherein the ligands are $C[CH_2P(C_6H_5)]_4$, tris[(2-diphenylphosphino)ethyl]phosphine, tris[(2-dimethylamino)ethyl]amine or N,N',N'',N''''-hexamethyl-triethylenetetraamine.

36. A process according to claim 1, wherein the ligands which are aliphatic, cycloaliphatic, cycloheteroaliphatic, aromatic or heteroaromatic compounds containing 2 to 30 carbon atoms (without the carbon atoms in the complex forming groups), the complex forming groups in the aliphatic compounds being in 1,2-, 1,3- or 1,4-position and, in the cyclic compounds, in 1,2- or 1,3-position, and the hetero atoms being selected from the group consisting of O, S and N, and the number of hetero atoms being preferably 1 or 2, and the complex forming groups are attached direct or through a $-CR_5R_6$ group to the molecule, and $R_5$ and $R_6$ are each independently of the other H, $C_1$-$C_4$alkyl, phenyl or benzyl.

37. A process according to claim 36, wherein the ligands contain complex forming groups of formula $-NR_1R_2$, $-PR_1R_2$, $-OPR_1R_2$, $-AsR_1R_2$ or $-SbR_1R_2$, $R_1$ and $R_2$ are each independently of the other $C_1$-$C_{12}$alkyl, $C_5$cycloalkyl or $C_6$cycloalkyl, phenyl or benzyl which are unsubstituted or substituted by $C_1$-$C_4$alkyl or $C_1$-$C_4$alkoxy.

38. A process according to claim 36, wherein the bidentate ligands have the formula I

$$R_1R_2X-Y-X'R_1R_2 \qquad (I),$$

wherein X and X' are each independently of the other N, P, As, Sb or $-OP$, $R_1$ and $R_2$ are each independently of the other be $C_1$-$C_{12}$alkyl, $C_5$cycloalkyl or $C_6$cycloalkyl, phenyl or benzyl which are unsubstituted or substituted by $C_1$-$C_4$alkyl or $C_1$-$C_4$alkoxy, Y is a linear or branched alkylene or alkenylene radical of 2 to 20 carbon atoms, which radical is unsubstituted or substituted by $C_1$-$C_6$alkoxy, $C_5$cycloalkyl or $C_6$cycloalkyl, $C_5$cycloalkoxy or $C_6$cycloalkoxy, phenyl, phenoxy, benzyl or benzyloxy, and the cyclic substituents are in turn substituted by $C_1$-$C_6$alkyl or $C_1$-$C_6$alkoxy, and the groups $R_1R_2X-$ and $R_1R_2X'-$ are in $\alpha,\beta$-, $\alpha,\gamma$- or $\alpha,\delta$-position in the alkylene or alkenylene radical.

39. A process according to claim 36, wherein the bidentate ligands have the formula II

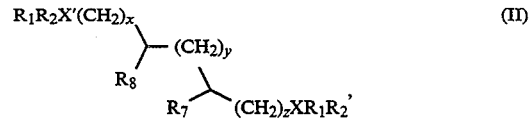

wherein X and X' are each independently of the other N, P, As, Sb or $-OP$, $R_1$ and $R_2$ are each independently of the other be $C_1$-$C_{12}$ alkyl, $C_5$cycloalkyl or $C_6$cycloalkyl, phenyl or benzyl which are unsubstituted or substituted by $C_1$-$C_4$alkyl or $C_1$-$C_4$alkoxy, x, y and z are each independently of one another 0 or 1, the sum of $x+y+z$ being 0, 1 or 2, $R_7$ and $R_8$, together with the radical to which they are attached, form a 5- or 6-membered cycloaliphatic radical or a 5- or 6-membered cycloheteroaliphatic radical containing one or two identical or different hetero atoms selected from the group consisting of O, S and $NR_9$, which radicals are unsubstituted or substituted by $C_1$-$C_6$alkyl or $C_1$-$C_6$alkoxy or halogen, $R_9$ is H, $C_1$-$C_6$alkyl, $C_1$-$C_8$acyl, phenyl or benzyl or phenyl or benzyl which are substituted by $C_1$-$C_6$alkyl or $C_1$-$C_6$alkoxy, and, if y is 0, $R_7$ and $R_8$, together with the radical to which they are attached, form a 6-membered aromatic or heteroaromatic radical or a 5-membered heteroaromatic radical, which radicals are unsubstituted or substituted by $C_1$-$C_6$alkyl or $C_1$-$C_6$alkoxy or halogen.

40. A process according to claim 1, wherein the ligands are bidentate strongly complexing ligands which are biphenylene or naphthylene which are substituted in the o,o'-positions by identical or different groups $-XR_1R_2$, wherein the substituents X are each independently of one another N, P, As, Sb or $-OP$, $R_1$ and $R_2$ are each independently of the other $C_1$-$C_{12}$alkyl, $C_5$cycloalkyl or $C_6$cycloalkyl, phenyl or benzyl which are unsubstituted or substituted by $C_1$-$C_4$alkyl or $C_1$-$C_4$alkoxy.

41. A process according to claim 40, wherein the bidentate strongly complexing ligands are 2,2'-diphenylphosphinobiphenyl or -binaphthyl or 2,2'-bicyclohexylphosphinobiphenyl or -binaphthyl.

42. A process according to claim 36, wherein the the bidentate ligands are ferrocenes of formulae III and IIIa

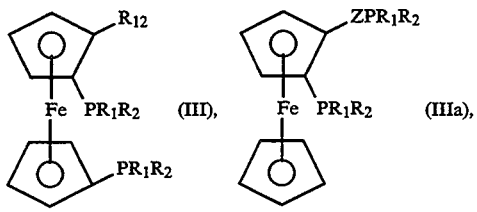

wherein $R_1$ and $R_2$ are each independently of the other $C_1$-$C_{12}$alkyl, $C_5$cycloalkyl or $C_6$cycloalkyl, phenyl or benzyl which are unsubstituted or substituted by $C_1$-$C_4$alkyl or $C_1$-$C_4$alkoxy, $R_{12}$ is H, $C_1$-$C_6$alkyl, $C_1$-$C_6$alkenyl, tri($C_1$-$C_6$alkyl)silyl, phenyl, benzyl, α-hydroxy- or α-[di($C_1$-$C_6$alkyl)amino]-$C_1$-$C_6$alkyl, and Z is methylene or $C_1$-$C_8$alkylidene.

43. A process according to claim 36, wherein the bidentate ligands are α,α'-bipyridyl which is unsubstituted or substituted by $C_1$-$C_4$alkyl, $C_1$-$C_4$alkoxy, F or Cl.

44. A process according to claim 36, wherein the bidentate ligands are bisoxazolidines of formula IV,

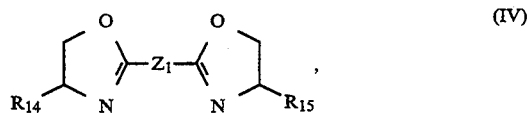

wherein $R_{14}$ and $R_{15}$ are identical or different and are H, linear or branched $C_1$-$C_6$alkyl, phenyl, ($C_1$-$C_6$ alkyl)-phenyl, benzyl or ($C_1$-$C_6$alkyl)benzyl, and $Z_1$ is a direct bond, methylene, $C_2$-$C_8$alkylidene, ethylene, 1,2-propylene or 1,2-phenylene.

45. A process according to claim 36, wherein the bidentate ligands are bisoxazolidines of formula V

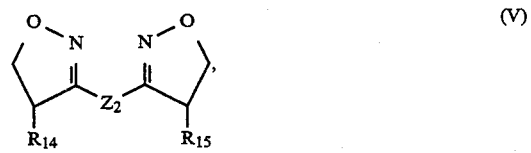

wherein $R_{14}$ and $R_{15}$ are identical or different and are H, linear or branched $C_1$-$C_6$alkyl, phenyl, ($C_1$-$C_6$alkyl)-phenyl, benzyl or ($C_1$-$C_6$alkyl)benzyl, and $Z_2$ is a direct bond, methylene, 1,2- or 1,3-phenylene, pyridine-2,6-diyl, ethylene, 1,2- or 1,3-propylene or 1,2-, 1,3-, 1,4- or 2,3-butylene or $C_2$-$C_8$alkylidene.

46. A process according to claim 1, wherein the ligand comprises two different strongly co-ordinating bidentate ligands, one bidentate strongly co-ordinating ligand and one monodentate strongly co-ordinating ligand, one bidentate strongly co-ordinating ligand and two monodentate weakly or strongly co-ordinating ligands, two different tridentate strongly co-ordinating ligands or one tridentate strongly co-ordinating ligand and three monodentate weakly or strongly co-ordinating ligands.

47. A process according to claim 15, wherein the metal salts contain a halide as nucelophilic anion.

48. A process according to claim 1, wherein the metal complex salts contain sulfate, phosphate, perchlorate, perbromate, periodate, antimonate, arsenate, nitrate, carbonate, the anion of a $C_1$-$C_8$carboxylic acid, sulfonates and phosphonates as non-nucleophilic anions.

49. A process according to claim 1, wherein the metal complex salts contain tetrafluoroborate, hexafluorophosphate, perchlorate or triflate as anions.

50. A process according to claim 1, wherein the metal complex salts have the formula VI $$[(Q)_m(M^{+n})(S)_o(L^{-1})_q]^{+(n-q)}(A^{-r})_{(n-q)/r} \qquad (VI),$$

wherein Q denotes identical or different strongly co-ordinating ligands, m is 0, or Q is a monodentate ligand and m is an integer from 1 to 8, Q is a bidentate ligand and m is an integer from 1 to 4, Q is a tridentate ligand and m is 1 or 2, or Q is a tetradentate ligand and m is 1 or 2, said monodentate, bidentate and tetradentate ligands containing one or more identical or different phosphino, phosphonite, arsino, or stibino groups or primary), secondary and/or tertiary amino groups and/or imino groups as complex forming groups, and said ligands form with the metal cation $M^{+n}$ a 5- to 7-membered ring; and n is an integer from 1 to 4; S is a weakly co-ordinating ligand selected from the group consisting of nitriles, aliphatic or aromatic alcohols, ketones, aldehydes, carboxylates, ethers, tris(trifluoromethyl)-phosphite, and water, and o is 0 or an integer from 1 to 6; L is halide, pseudohalide, $C_1$-$C_8$alcoholate or unsubstituted or $C_1$-$C_4$alkyl-substituted phenolate, secondary amide of 2 to 12 carbon atoms, bis[(tri-$C_1$-$C_6$alkyl)silyl-]amide or unsubstituted or $C_1$-$C_4$alkyl-substituted cyclopentadienyl, and q is 0 or an integer from 1 to 4; A is an anion of an oxyacid, $BF_4$, $PF_6$, $AsF_6$ or $SbF_6$, and r is an integer from 1 to 3, such that the the sum of (m × the number of possible co-ordination points on the ligand Q)+o+q is an integer from 2 to 8 and the sum of (m × the number of possible co-ordination points on the ligand Q)+o is at least 2.

51. A process according to claim 1, wherein the solvent is selected from the group consisting of halogenated aliphatic hydrocarbons, aromatic hydrocarbons, ethers and nitriles.

52. A process according to claim 1, wherein the protected sugar and the aglycon are used in equimolar amounts.

53. A process according to claim 1, wherein the orthoester is used in amounts of 1.2 to 10 equivalents per equivalent of protected sugar.

54. A process according to claim 1, wherein the orthoester is used in amounts of 1.2 to 5 equivalents per equivalent of protected sugar.

55. A process according to claim 1, wherein the reaction temperature is in the range from −20° to +250° C.

56. A process according to claim 1, wherein the reaction temperature is in the range from 10° to 200° C.

57. A process according to claim 36 wherein the aliphatic, cycloaliphatic, cycloheteroaliphatic, aromatic or heteroaromatic compounds contain from 2 to 20 carbon atoms, excluding the carbon atoms in the complex forming groups.

58. A process according to claim 1, which comprises chemically binding the water of reaction or removing it continuously from the reaction mixture.

59. A process according to claim 1, which comprises charging the protected sugar and the catalyst in a solvent at room temperature to the reactor and then adding the aglycon and an orthoester, then stirring the mixture at room temperature up to the reflux temperature of the solvent.

60. A process according to claim 59, which comprises the use of an orthoester of an alcohol which is simultaneously used as aglycon.

61. A process according to claim 1, which comprises charging the protected sugar and the aglycon in a solvent to the reactor and then adding the catalyst, followed by the addition of the water absorbent in a Soxhlet apparatus in a jacket, then heating the reaction mixture under reflux.

62. A process according to claim 1, which comprises charging the protected sugar and the aglycon in a solvent to the reactor and then adding the catalyst, using an apparatus with water separator, then heating the reaction mixture under reflux and removing the water of reaction by distillation as an azeotrope until the reaction is complete.

* * * * *